US008673315B2

(12) United States Patent
Roy et al.

(10) Patent No.: US 8,673,315 B2
(45) Date of Patent: Mar. 18, 2014

(54) METHOD FOR PRODUCING VACCINAL VIRAL STRAIN OF A VIRUS OF THE REOVIRIDAE FAMILY

(75) Inventors: Polly Roy, London (GB); Mark Boyce, Ashtead (GB)

(73) Assignee: London School of Hygiene & Tropical Medicine, London (GB)

( * ) Notice: Subject to any disclaimer, the term of this patent is extended or adjusted under 35 U.S.C. 154(b) by 619 days.

(21) Appl. No.: 12/744,041

(22) PCT Filed: Nov. 26, 2008

(86) PCT No.: PCT/GB2008/003945
§ 371 (c)(1),
(2), (4) Date: Aug. 13, 2010

(87) PCT Pub. No.: WO2009/068870
PCT Pub. Date: Jun. 4, 2009

(65) Prior Publication Data
US 2010/0322971 A1    Dec. 23, 2010

Related U.S. Application Data

(60) Provisional application No. 60/989,991, filed on Nov. 26, 2007, provisional application No. 61/058,716, filed on Jun. 4, 2008.

(51) Int. Cl.
*A61K 39/125*     (2006.01)
*A61K 39/12*      (2006.01)
(52) U.S. Cl.
USPC ............... 424/215.1; 424/204.1; 424/205.1
(58) Field of Classification Search
None
See application file for complete search history.

(56) References Cited

U.S. PATENT DOCUMENTS

2002/0164770 A1    11/2002   Hoffmann

FOREIGN PATENT DOCUMENTS

JP    2007-215466 A    8/2007

OTHER PUBLICATIONS

Zou and Brown Stable Expression of the Reovirus p.,2 Protein in Mouse L Cells Complements the Growth of a Reovirus ts Mutant with a Defect in Its M1 Gene. Virol. 1996; 217: 42-48.*
Roy, P. "Chapter 54: Orbiviruses" in Knipe, David M.; Howley, Peter M., Fields Virology, 5th Edition, Copyright (c) 2007 Lippincott Williams & Wilkins.*
Roner and Jaklik (Reovirus reverse genetics: Incorporation of the CAT gene into the reovirus genome. Proc. Nat'l. Acad. Sci. 2001; 98(14):8036-8041.*
Schiff, et al. "Chapter 52: Orthoreoviruses and Their Replication" in Knipe, David M.; Howley, Peter M., Fields Virology, 5th Edition, Copyright (c) 2007 Lippincott Williams & Wilkins.*
Hawley-Nelson and Ciccarone, Curr. Prot. Cell Biol. 2003; 20.6.1-20.6.17.*
Roner and Jaklik Reovirus reverse genetics: Incorporation of the CAT gene into the reovirus genome. PNAS, 2001; 98(14): 8036-8041.*
Boyce and Roy Recovery of Infectious Bluetongue Virus from RNA. J. Virol. 2007; 81(5): 2179-2186.*

(Continued)

*Primary Examiner* — Jeffrey Stucker
*Assistant Examiner* — Stuart W Snyder
(74) *Attorney, Agent, or Firm* — Klarquist Sparkman, LLP

(57) ABSTRACT

The invention relates to a method for producing a modified viral strain of a virus which is a member of the Reoviridae family and, in particular, relates to vaccinal viral strains of the Orbivirus genus.

14 Claims, 20 Drawing Sheets

(56) References Cited

OTHER PUBLICATIONS

Hawley-Nelson and Ciccarone Curr. Prot. Cell Biol. 2003; 20.6.1-20.6.17.*

Widjojoatmodjo, et al. Classical Swine Fever VirusErns Deletion Mutants: trans-Complementation and Potential Use as Nontransmissible, Modified, Live-Attenuated Marker Vaccines. J. Virol. 2000: 74(7): 2973-2980.*

Boyce and Roy, "Recovery of Infectious Bluetongue Virus from RNA," *J. Virol.* 81:2179-2186, 2007.

Boyce et al., "Development of Reverse Genetics Systems for Bluetongue Virus: Recovery of Infectious Virus from Synthetic RNA Transcripts," *J. Virol.* 82:8339-8348, 2008.

Kobayashi et al., "A Plasmid-Based Reverse Genetics System for Animal Double-Stranded RNA Viruses," *Cell Host Microbe* 1:147-157, 2007.

Komoto et al., "Reverse Genetics System for Introduction of Site-Specific Mutations Into the Double-Stranded RNA Genome of Infectious Rotavirus," *Proc. Natl. Acad. Sci. USA* 103:4646-4651, 2006.

Roner and Joklik, "Reovirus Reverse Genetics: Incorporation of the *CAT* Gene Into the Reovirus Genome," *Proc. Natl. Acad. Sci. USA* 98:8036-8041, 2001.

* cited by examiner

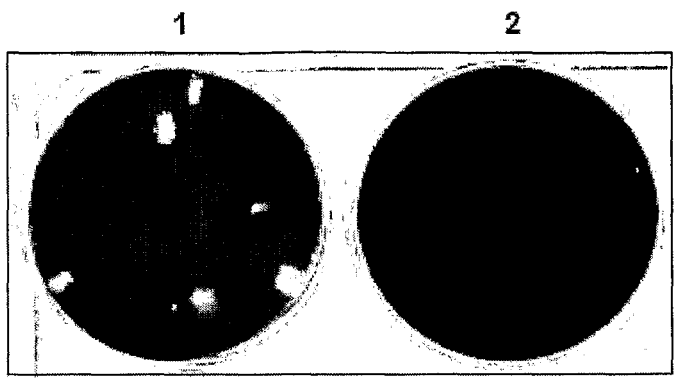
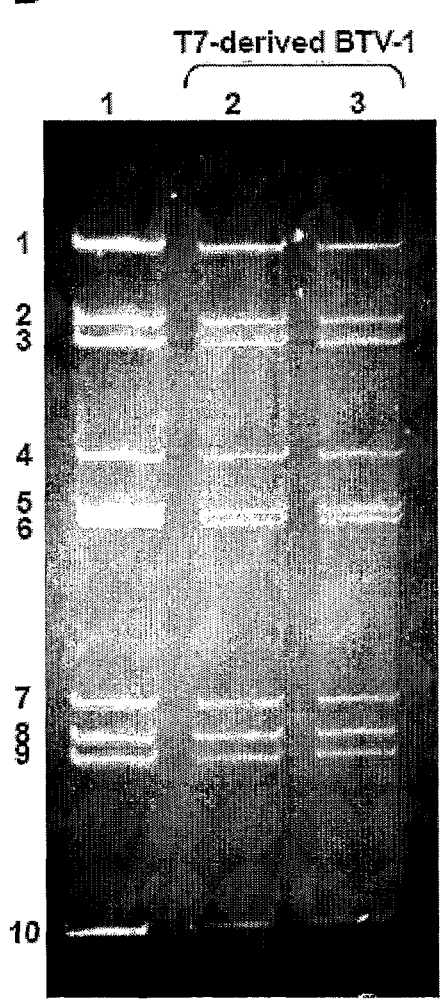
Figure 8

Wild type BTV1
BTV1 delta VP6

1
2
3
4
5, 6
7
8, 9
10
S9 delta

B

BTV1 delta VP6
Wild type BTV1
No template 1882
1489
925
421

Growth of BTV1 delta VP6 on BSR Cells wt BTV1 + BSR
BTV1 delta VP6 + BSR

B

Growth of BTV1 delta VP6 on C6/36 Cells wt BTV1 + C6/36
BTV1 delta VP6 + C6/36

A / B: BTV1 S10GFP infected

C / D: Mock infected

SEQUENCE LISTING

<160> NUMBER OF SEQ ID NOS: 25

<210> SEQ ID NO 1
<211> LENGTH: 40
<212> TYPE: DNA
<213> ORGANISM: Bluetongue virus

<400> SEQUENCE: 1
gagttaatta agcggccgca gtttagaatc ctcagaggtc          40

<210> SEQ ID NO 2
<211> LENGTH: 41
<212> TYPE: DNA
<213> ORGANISM: Bluetongue virus

<400> SEQUENCE: 2
ctactagtgg ctgctgtggt agcgctgctg acatcagttt g          41

<210> SEQ ID NO 3
<211> LENGTH: 41
<212> TYPE: DNA
<213> ORGANISM: Bluetongue virus

<400> SEQUENCE: 3
caaactgatg tcagcagcgc taccacagca gccactagta g          41

<210> SEQ ID NO 4
<211> LENGTH: 43
<212> TYPE: DNA
<213> ORGANISM: Bluetongue virus

<400> SEQUENCE: 4
gatttaccag gtgtgatgag atctaactac gatgttcgtg aac          43

<210> SEQ ID NO 5
<211> LENGTH: 42
<212> TYPE: DNA
<213> ORGANISM: Bluetongue virus

<400> SEQUENCE: 5
cgaacatcgt agttagatct catcacacct ggtaaatcgg gc          42

<210> SEQ ID NO 6
<211> LENGTH: 22
<212> TYPE: DNA
<213> ORGANISM: Bluetongue virus

<400> SEQUENCE: 6
ggagaaggct gcattcgcat cg          22

<210> SEQ ID NO 7
<211> LENGTH: 44
<212> TYPE: DNA
<213> ORGANISM: Bluetongue virus

<210> SEQ ID NO 7

<400> SEQUENCE: 7
ctcatcctca ctgcgtcatt atatgattgt tttttcatca cttc          44

<210> SEQ ID NO 8
<211> LENGTH: 29
<212> TYPE: DNA
<213> ORGANISM: Bluetongue virus

<400> SEQUENCE: 8
atgacagcag acgtgctaga ggcggcatc                            29

<210> SEQ ID NO 9
<211> LENGTH: 25
<212> TYPE: DNA
<213> ORGANISM: Bluetongue virus

<400> SEQUENCE: 9
gcgttcaagc atttcgtaag aagag                                25

<210> SEQ ID NO 10
<211> LENGTH: 24
<212> TYPE: DNA
<213> ORGANISM: Bluetongue virus

<400> SEQUENCE: 10
ccgtacgaac gatttatatc cagc                                 24

<210> SEQ ID NO 11
<211> LENGTH: 21
<212> TYPE: DNA
<213> ORGANISM: Bluetongue virus

<400> SEQUENCE: 11
tactaattca gaacgcgcgc c                                    21

<210> SEQ ID NO 12
<211> LENGTH: 45
<212> TYPE: DNA
<213> ORGANISM: Bluetongue virus

<400> SEQUENCE: 12
cgggatccta atacgactca ctatagttaa aaaatccttg agtca          45

<210> SEQ ID NO 13
<211> LENGTH: 38
<212> TYPE: DNA
<213> ORGANISM: Bluetongue virus

<400> SEQUENCE: 13
catgggatcc ggaccgtctc cgtaagtgta aaatcccc                  38

<210> SEQ ID NO 14
<211> LENGTH: 20
<212> TYPE: DNA
<213> ORGANISM: Bluetongue virus

<400> SEQUENCE: 14
cagcttctcc aatctgctgg                                      20

<210> SEQ ID NO 15
<211> LENGTH: 53
<212> TYPE: DNA
<213> ORGANISM: Bluetongue virus -continued

```
<400> SEQUENCE: 15
ctaggaattc taatacgact cactatagtt aaaaaatcgc atatgtcagc tgc          53

<210> SEQ ID NO 16
<211> LENGTH: 38
<212> TYPE: DNA
<213> ORGANISM: Bluetongue virus

<400> SEQUENCE: 16
cagtgaattc gtctccgtaa gtgtaaaatc gccctacg                           38

<210> SEQ ID NO 17
<211> LENGTH: 50
<212> TYPE: DNA
<213> ORGANISM: Bluetongue virus

<400> SEQUENCE: 17
cggaattcta atacgactca ctatagttaa aaagtgtcgc tgccatgcta              50

<210> SEQ ID NO 18
<211> LENGTH: 23
<212> TYPE: DNA
<213> ORGANISM: Bluetongue virus

<400> SEQUENCE: 18
gtaagtgtgt agtatcgcgc acc                                           23

<210> SEQ ID NO 19
<211> LENGTH: 23
<212> TYPE: DNA
<213> ORGANISM: Bluetongue virus

<400> SEQUENCE: 19
taatacgact cactatagtt aaa                                           23

<210> SEQ ID NO 20
<211> LENGTH: 13
<212> TYPE: DNA
<213> ORGANISM: Bluetongue virus

<400> SEQUENCE: 20
acttactgag acg                                                      13

<210> SEQ ID NO 21
<211> LENGTH: 30
<212> TYPE: DNA
<213> ORGANISM: Bluetongue virus

<400> SEQUENCE: 21
gtggctgctg tggttgcgct gctgacatca                                    30

<210> SEQ ID NO 22
<211> LENGTH: 30
<212> TYPE: DNA
<213> ORGANISM: Bluetongue virus

<400> SEQUENCE: 22
atagcggcgg ttgttgctct gttgacatca                                    30

<210> SEQ ID NO 23
<211> LENGTH: 31
<212> TYPE: DNA
<213> ORGANISM: Bluetongue virus
```

```
<400> SEQUENCE: 23
agtggctgct gtggttgcgc tgctgacatc a                              31

<210> SEQ ID NO 24
<211> LENGTH: 31
<212> TYPE: DNA
<213> ORGANISM: Bluetongue virus

<400> SEQUENCE: 24
agtggctgct gtggtagcgc tgctgacatc a                              31

<210> SEQ ID NO 25
<211> LENGTH: 28
<212> TYPE: DNA
<213> ORGANISM: Bluetongue virus

<400> SEQUENCE: 25
caggtgtgat gagatctaac tacgatgt                                  28
```

METHOD FOR PRODUCING VACCINAL VIRAL STRAIN OF A VIRUS OF THE REOVIRIDAE FAMILY

CROSS REFERENCE TO RELATED APPLICATIONS

This is the U.S. National Stage of International Application No. PCT/GB2008/003945 filed Nov. 26, 2008, which was published in English under PCT Article 21 (2), which in turn claims the benefit of U.S. Provisional Application No. 61/058,716, filed Jun. 4, 2008 and U.S. Provisional Application No. 60/989,991, filed Nov. 26, 2007.

FIELD

The invention relates to a method for producing a modified viral strain of a virus which is a member of the Reoviridae family and, in particular, relates to vaccinal viral strains of the Orbivirus genus.

BACKGROUND

Reoviridae viruses, which have a genome consisting of double stranded RNA (dsRNA), cause many diseases. Orbiviruses which are viruses of the Reoviridae family, also cause widespread disease. Examples of Orbiviruses are African Horse Sickness Virus (AHSV), Epizootic Hemorrhagic Disease Virus (EHDV) and Bluetongue virus (BTV).

African Horse Sickness Virus (AHSV), Epizootic Hemorrhagic Disease Virus (EHDV) and Bluetongue virus (BTV) are non-contagious, viral diseases of ruminants and are commonly spread by insect vectors. AHSV commonly affects horses, mules, donkeys and zebras; EHDV commonly affects deer, cattle and sheep; and BTV commonly affects cattle, sheep, goats, buffalo, deer, dromedaries and antelope.

Bluetongue virus (BTV) is an insect-vectored emerging pathogen of wild ruminants and livestock which has had a severe economic impact on European agriculture. BTV causes disease in sheep, goats, and cattle with mortality reaching 70% in some breeds of sheep. BTV is transmitted between mammalian hosts by several species of biting midges in the *Culicoides* genus, which determine its geographic range. BTV is endemic in many tropical and subtropical countries, but since 1998 incursions of BTV into mainland Europe have been common events, reaching as far north as the UK in 2007. Molecular epidemiology studies show that six different serotypes (BTV1, 2, 4, 8, 9, and 16) have been introduced into mainland Europe since 1998, on at least eight separate occasions, via at least three different routes, involving new introductions in most years since 1998. The probable direct causes for the increased range of BTV are the increased distribution and size of insect vector populations, and the transmission of BTV by novel vector species, which are abundant in central and northern Europe. The existence of undiagnosed infections of livestock or wild ruminants coupled with the rapid spread over large distances through movement of the insect vector has resulted in a failure to prevent BTV becoming endemic in Europe. Thus, BTV now represents a considerable threat to livestock in all European countries. Four BTV serotypes are now common in Europe and have resulted in the deaths of 1.8 million animals.

The control of BTV through vaccination has been attempted in Europe using both live and inactivated vaccines to a small number of serotypes. Both types of vaccine have provided some protection for regions in Europe, but have known drawbacks. Live attenuated BTV vaccines suffer from a number of drawbacks: 1) under-attenuation leading to the development of typical bluetongue clinical symptoms; 2) reversion to virulence or re-assortment with wild-type virus followed by spread via the insect vector; 3) inability to distinguish vaccinated animals from naturally infected animals precluding the use of a differentiation of infected from vaccinated animals (DIVA) strategy; and 4) time delay to produce attenuated strains of newly circulating serotypes.

Inactivated vaccines have been used to control BTV2 and BTV4 in Europe. These suffer from the high production costs associated with inactivation, confirming the inactivation of every batch, and low immunogenicity.

It has previously been reported by the inventors that BTV ssRNA is infectious without the use of a helper virus and infectious BTV can be recovered from cells (Boyce, M. and Roy, P. 2007). This document is incorporated herein in its entirety.

SUMMARY

The present invention aims to reduce or eliminate some or all of the known drawbacks associated with modifying a viral strain of a virus which is a member of the Reoviridae family, and in particular with the generation of live attenuated vaccines.

The present invention provides a method for producing a vaccinal viral strain of a virus which is a member of the Reoviridae family, the method comprising:
  introducing a mutation into the Reoviridae virus so that the function of an essential gene is destroyed;
  transfecting a cell with viral single stranded RNA (ssRNA) derived from the virus genome and comprising the mutation; and
  culturing the transfected cell under suitable conditions in order to lead to the production of the vaccinal viral strain,
  wherein the cell complements the function of the essential viral gene thereby allowing the vaccinal viral strain to replicate in the cell.

The term "vaccinal viral strain" means a viral strain that is suitable for being used in a vaccine for immunising the particular host that is normally affected by the wild-type virus. A vaccinal viral strain is one that is non-pathogenic and cannot cause infection. Therefore, it does not cause the disease that is normally associated with the wild-type virus. The concept of vaccinal viral strains is well known to those skilled in the art. For example, wild-type viruses can be attenuated or inactivated so that they generate an immune response in a host immunised with the attenuated or inactivated virus without causing full blown infection. This allows a host to mount an effective immune response if the host is exposed to the wild-type virus.

In the present invention, the virus can be any virus which is a member of the Reoviridae family. Preferably, the virus is a member of the Rotavirus, Coltivirus or Orbivirus genus. More preferably, the virus is a member of the Orbivirus genus. Even more preferably, the virus is bluetongue virus (BTV), African horse sickness virus (AHSV) or epizootic hemorrhagic disease virus (EHDV). Most preferably, the virus is bluetongue virus (BTV).

Many viruses have a number of different serotypes. For example, BTV has 24 different serotypes. Different serotypes can have slightly different proteins and may even differ in the number of genes contained in the different genomes. Further, in the future, as yet undiscovered serotypes are likely to develop. Therefore, the present invention is intended to encompass any possible serotype of virus, known or as yet unknown, which falls within the definition of the above categories, for example, a BTV.

The term "essential gene" means a gene which is essential for the virus to be pathogenic. When the function of the essential gene is destroyed, the resulting vaccinal viral strain is non-pathogenic. The function of the essential gene is destroyed by introducing a mutation into the gene. The function of at least one essential gene should be destroyed. Preferably, the function of more than one essential gene is destroyed. This helps to ensure that the virus does not revert back to a pathogenic phenotype. Preferably, the mutation in the, or each, essential gene is an extensive mutation which affects a large part of the sequence of the essential gene. Again, this helps to ensure that the virus does not revert back to a pathogenic phenotype. The mutation can be in any essential gene which will allow the virus to be converted to a non-pathogenic phenotype. Preferably, the mutation is introduced in an enzymatic protein, for example, in the polymerase, helicase or capping enzymes. Alternatively, non-structural proteins can be inactivated. This allows the use of a DIVA strategy. This is the differentiation of infected animals from vaccinated animals. For example, if the gene encoding NS1 is deleted in a BTV, the vaccinal strain will not express NS1 in the vaccinated animal. Therefore, no antibody response to NS1 will be generated in the vaccinated animal. This differs from a normal infection where NS1 is expressed and an antibody response is made in the animal. During surveillance, the detection of the antibody to NS1 demonstrates that the animal was infected with wildtype BTV, rather than the vaccine strain. In addition, a gene encoding a marker antigen can be introduced into the genome. This would be an unambiguous antigenic marker demonstrating that the animal has been vaccinated.

The mutation can be introduced into the gene or each gene in any suitable way. For example, the mutation can be introduced into the genome of the virus. A ssRNA transcript produced from this genome will also contain the mutation. Alternatively, the mutation could be introduced directly into the ssRNA. This can be done, for example, by replacing a section of the ssRNA with an artificially created ssRNA corresponding to the replaced section but also comprising a mutation. In one embodiment, the ssRNA used to transfect the cell can be completely artificially produced. This completely artificially produced ssRNA will correspond to the entire genome of the virus with a mutation in an essential gene or genes. For example, in one embodiment, a cDNA clone can be made of one part of the viral genome.

Alternatively, a cDNA clone can be made of the entire viral genome. Mutations can then be introduced into the cDNA clones, for example, to produce a library of cDNA clones with various different mutations. Transcripts from these cDNA clones can then be used as the ssRNA used to transfect a cell. Therefore, one part of the ssRNA may be created from a cDNA clone. Alternatively, the entire ssRNA used to transfect the cell may be created from a cDNA clone.

The mutation can be any suitable mutation which destroys the function of the gene. The mutation can be, for example, a deletion or an insertion mutation so that a non-functional protein is produced by the mutated gene. Preferably, a large deletion mutation is introduced into the virus.

The cell which is transfected with ssRNA can be any cell which is suitable for being transfected with ssRNA and for culturing viral strains. The cell is a viral permissive cell. Preferably, the cell is a BHK 21 cell, a Vero cell, a 293T cell, a BSR cell (a clone of a particular BHK 21 cell), a HeLa cell, a C6/36 cell (a mosquito cell line derived from *Aedes albopictus*), or a KC cell (a midge cell line derived from the natural insect vector *Culicoides sonorensis*). More preferably, the cell is a BSR cell.

The ssRNA used to transfect the cell is a transcript of the genome of the virus and also comprises the mutation. This transcript can be obtained directly from the dsRNA genome of the virus which contains a mutation. Alternatively, the transcript can be obtained indirectly from the viral genome. For example, the transcript can be produced from a cDNA clone of the viral genome, the cDNA clone comprising a mutation. In Reoviridae viruses, for example BTV, viral ssRNA is synthesised in the cytoplasm of the infected cell by viral particles where it serves as mRNAs for viral protein synthesis and as a template for the synthesis of new genomic dsRNA. The ssRNA of the present invention also performs these functions and so the mutation in the ssRNA is incorporated into the vaccinal viral strain during synthesis of the dsRNA genome.

The ssRNA may be modified to comprise desired immunologically relevant proteins of the virus. For example, when the virus is BTV, the ssRNA preferably encodes VP2 and VP5 from a serotype of interest. In some embodiments, the ssRNA may encode a variety of immunologically important proteins from a number of different viral serotypes. Such a ssRNA may then be used to vaccinate against a number of different viral serotypes.

Preferably the viral ssRNA used to transfect the cell is isolated ssRNA. This means the ssRNA is substantially free from other viral components, for example, virus particles, viral dsRNA and viral proteins.

The transfected cell can be cultured in any suitable way and under any suitable conditions to allow production of the vaccinal viral strain. Such methods of culturing cells are well known to those skilled in the art.

The step of transfecting the cell preferably comprises 2 or more transfection steps, wherein:
(1) a first transfection step comprises transfecting the cell with ssRNA encoding at least the components required for assembly of the inner layer of the viral capsid; and
(2) a second transfection step comprises transfecting the cell with ssRNA which is a transcript of the viral genome and comprises the mutation, and therefore encodes all the components required for assembly of the virus.

It has been found that by performing 2 transfections that the level of virus produced is increased ~10 fold. Furthermore, by ensuring that at least one viral component required for genome packaging is not encoded by the ssRNA transfected in the first transfection step, the level of virus produced is increased ~100 fold above that achieved when there is only a single transfection step. When working with BTV, it is preferred that at least one of viral components VP2, VP5, VP7 and NS3 is not encoded by the ssRNA transfected in the first transfection step. Preferably all of viral components VP2, VP5, VP7 and NS3 are omitted during the first transfection step.

It is preferred that there is a time gap between the first and second transfection steps so that there is sufficient time for assembly of the inner layer of the viral capsid. Preferably there is at least 6 hours, more preferably 12 hours and most preferably 18 hours between the first and second transfection steps.

The cell complements the function of the essential viral gene. This means that the cell has been modified so that it contains a copy of the inactivated essential gene. As a result the protein produced by the essential gene is expressed from mRNA from the cell rather than from the ssRNA of the virus and so the function of this gene is complemented by the cell.

This ensures that all the essential proteins that are necessary for replication of the virus are present within the cell. Therefore, the vaccinal viral strain can freely replicate within the cell. However, if the vaccinal viral strain infects a cell other than the complementing cell, the protein product of the essential gene will not be present and so the vaccinal viral strain will not be able to repeatedly replicate. The vaccinal viral strain will undergo a single replication cycle, for example, in a vaccinated host. When the function of more than one essential gene is destroyed, the cell complements the function of each essential viral gene.

Preferably, the method for producing a vaccinal viral strain further comprises isolating the vaccinal viral strain from the cell. This can be done in any suitable way. Such ways are well known to those skilled in the art. For example, vaccinal viral strains can be isolated from viral plaques.

The present invention also provides an isolated viral ssRNA derived from the genome of a virus which is a member of the Reoviridae family wherein the ssRNA comprises a mutation which destroys the function of an essential gene, and wherein the viral ssRNA is suitable for use in the above method for transfecting a cell.

The present invention further provides a vaccinal viral strain produced by the method described above.

The present invention also provides a cell expressing an essential gene of a Reoviridae virus, which enables the replication of a vaccinal viral strain from the ssRNA of the present invention.

The present invention provides the cell of the present invention, infected with the ssRNA of the present invention.

The present invention also provides the vaccinal viral strain of the present invention for use in therapy.

The present invention also provides the isolated viral ssRNA of the present invention for use in therapy.

The present invention also provides the vaccinal viral strain of the present invention for use in vaccinating an animal against a Reoviridae virus.

The present invention also provides the isolated viral ssRNA of the present invention for use in vaccinating an animal against a Reoviridae virus.

The present invention also provides a method for vaccinating an animal against a Reoviridae virus comprising delivering an effective amount of the vaccinal viral strain of the present invention to the animal.

The present invention also provides a method for vaccinating an animal against a Reoviridae virus comprising delivering an effective amount of the isolated viral ssRNA of the present invention to the animal.

Since isolated viral ssRNA from Reoviridae viruses is infectious, it is possible to use the isolated viral ssRNA itself in vaccinating an animal. The ssRNA can be introduced into a cell or cells of the animal in any suitable way, where it will be transcribed by the cell or cells. This will produce viral proteins and may lead to the production of viral particles. However, since the function of an essential gene in the ssRNA from the virus is destroyed, the viral ssRNA will not be able to produce a fully functional virus particle. At most, the virus will be able to complete one replication cycle, depending on the identity of the essential gene that is mutated.

When vaccination takes place, the animal to be vaccinated will vary depending on the identity of the Reoviridae virus and the particular animals that it infects. When the virus is AHSV, the animal is selected from horses, mules, donkeys or zebras. When the virus is EHDV, the animal is selected from deer, cattle or sheep. When the virus is BTV, the animal is selected from cattle, sheep, goats, buffalo, deer, dromedaries and antelope.

The present invention also provides a pharmaceutical composition comprising the vaccinal viral strain of the present invention in combination with a pharmaceutically acceptable carrier, adjuvant or vehicle.

The present invention also provides a pharmaceutical composition comprising the isolated viral ssRNA of the present invention in combination with a pharmaceutically acceptable carrier, adjuvant or vehicle.

Pharmaceutically acceptable carriers, adjuvants and vehicles are well known to those skilled in the art. For example, pharmaceutically acceptable carriers, adjuvants and vehicles that may be used, include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, sodium carboxymethylcellulose, polyacrylates, waxes, polyethylene-polyoxypropylene-block polymers, polyethylene glycol and wool fat.

The vaccinal viral strain, isolated viral ssRNA or pharmaceutical composition of this invention may be administered orally, parenterally, or by inhalation. Preferably the vaccinal viral strain, isolated viral ssRNA or pharmaceutical composition is administered by injection. The vaccinal viral strain, isolated viral ssRNA or pharmaceutical composition of this invention may be formulated with any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The vaccinal viral strain, isolated viral ssRNA or pharmaceutical composition may be in the form of an injectable preparation, for example, as an injectable aqueous or oleaginous suspension. This suspension may be formulated according to techniques known in the art using suitable dispersing or wetting agents (such as, for example, Tween 80® surfactant) and suspending agents. The injectable preparation may also be an injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono-or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or a similar alcohol as described in the Pharmacopoea Helvetica.

The vaccinal viral strain, isolated viral ssRNA or pharmaceutical composition may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The amount of vaccinal viral strain to be delivered to an animal can be determined using standard techniques; however, generally, the amount to be delivered should be in the range of 10,000 to 1,000,000,000 infectious units/ml.

The present invention also provides a kit comprising the isolated ssRNA of the above method and a cell that complements the essential gene mutated in the ssRNA.

The present invention also provides a screening method for identifying essential genes in a virus which is a member of the Reoviridae family, the method comprising:
introducing a mutation into the Reoviridae virus so that the function of a gene is destroyed;
transfecting a cell with viral ssRNA derived from the virus genome and comprising the mutation; and
culturing the transfected cell under suitable conditions,
wherein the viral gene is not an essential gene if the virus produced after culturing the transfected cell is pathogenic.

The present invention also provides a method for producing a modified viral strain of a virus which is a member of the Reoviridae family, the method comprising:
introducing a modification into the Reoviridae virus;
transfecting a cell with viral single stranded RNA (ssRNA) derived from the virus genome and comprising the modification; and
culturing the transfected cell under suitable conditions in order to lead to the production of the modified viral strain,
wherein the cell allows the modified viral strain to replicate in the cell.

The method of producing a modified viral strain is as defined above with respect to the method for producing the vaccinal viral strain. However, the viral strain may be modified in any manner. For example, the viral strain may be modified by adding one or more genes to the genome, deleting one or more genes from the genome, changing control sequences within the genome, etc. Furthermore, provided that the function of an essential gene is not destroyed, any suitable cell can be used for production of the modified virus.

As indicated above, it is preferred that the step of transfecting the cell comprises 2 or more transfection steps, wherein:
(1) the first transfection step comprises transfecting the cell with ssRNA encoding at least the components required for assembly of the inner layer of the viral capsid; and
(2) the second transfection step comprising transfecting the cell with ssRNA which is a transcript of the viral genome and also comprising the modification, and therefore encodes all the components required for assembly of the virus.

Preferred features of performing the 2 step transfection are as defined above.

Preferably, the method for producing the modified viral strain further comprises isolating the viral strain from the cell.

The present invention also provides an isolated viral ssRNA derived from the genome of a virus which is a member of the Reoviridae family wherein the ssRNA comprises a modification, and wherein the viral ssRNA is suitable for use in the above method for transfecting a cell.

The present invention further provides a modified viral strain produced by the method described above.

The present invention also provides the modified viral strain of the present invention for use in therapy.

The present invention also provides the isolated modified viral ssRNA of the present invention for use in therapy.

The present invention also provides a pharmaceutical composition comprising the modified viral strain of the present invention in combination with a pharmaceutically acceptable carrier, adjuvant or vehicle.

The present invention also provides a pharmaceutical composition comprising the isolated modified viral ssRNA of the present invention in combination with a pharmaceutically acceptable carrier, adjuvant or vehicle.

BRIEF SUMMARY OF THE DRAWINGS

The invention will now be described in detail, by way of example, with reference to the figures in which:

FIG. 1 shows reassortant progeny genomes recovered from the co-transfection of BSR cells with core-derived transcripts from two serotypes of BTV. Genomic dsRNA run on 9% non-denaturing polyacrylamide gels. (A). DsRNA from rescued BTV derived by the co-transfection of BSR cells with co-transcribed BTV-1 and BTV-9 transcripts. Lanes 1-3, plaque-purified viruses containing genome segments from both parental transcript preparations. Arrows indicate segments from the parent which has contributed the least number of segments. BTV-1 dsRNA and BTV-9 dsRNA marker lanes indicated. (B). DsRNA from rescued BTV derived by the co-transfection of BSR cells with BTV-1 and BTV-9 transcripts mixed after preparation. Lanes 1-2, plaque-purified viruses containing genome segments from both parental transcript preparations. Arrows indicate segments from the parent which has contributed the least segments. BTV-1 dsRNA and BTV-9 dsRNA marker lanes indicated.

FIG. 3 shows reassortant progeny genomes containing the plasmid-derived BTV-10 segment 10. (A). Genomic dsRNA run on a 9% non-denaturing polyacrylamide gel, extracted from BTV recovered from the co-transfection of BSR cells with BTV-10 segment 10 T7 transcript and core-derived BTV-1 transcripts. Lanes 1-5, viral dsRNA derived from plaques recovered. Lanes 1, 2, and 5, reassortants with arrows indicating the faster migrating BTV-10 segment 10 genome segment. Lanes 3 and 4, wildtype BTV-1. BTV-1 dsRNA and BTV-10 dsRNA marker lanes indicated. (B-D). Sequence electropherograms of segment 10 RT-PCR products. Segment 10 target sequences from total viral dsRNA were amplified by RT-PCR using primers BTV10_S10_259F and BTV10_S10_611R. Amplified targets were sequenced using BTV10_S10_259F. (B; SEQ ID NO: 21). BTV-10. (C; SEQ ID NO: 21). BTV-1 containing the introduced BTV-10 segment 10. (D; SEQ ID NO: 22). BTV-1.

FIG. 4 shows reassortant progeny genomes containing the plasmid-derived BTV-10 segment 10 with an Introduced Marker Mutation. (A). Genomic dsRNA from plaques containing BTV-10 segment 10 with an introduced HaeII site, run on a 9% non-denaturing polyacrylamide gel. Lanes 1-3, viral dsRNA from three plaque purified reassortants containing the faster migrating BTV-10 segment 10. BTV-1 dsRNA and BTV-10 dsRNA marker lanes indicated. (B). HaeII digestion of segment 10 RT-PCR products. HaeII-digested RT-PCR products amplified from genomic dsRNA using segment 10 primers BTV10_S10_259F and BTV10_S10_611R, and separated on 2% agarose gels. U=undigested RT-PCR product, D=HaeII digested RT-PCR product. Lanes 1, no template, lanes 2, BTV-10, lanes 3, reassortant with BTV-10 segment 10 introduced, lanes 4, reassortant with HaeII site-containing BTV-10 segment 10 introduced, lanes 5, BTV-1. M=StyI-digested phage λ DNA markers, with sizes in by indicated. Size of RT-PCR product and digest fragments indicated on left in bp. (C and D). Sequence electropherograms of segment 10 RT-PCR products. Segment 10 target sequences from total viral dsRNA were amplified by RT-PCR using primers BTV 10_S10_238F and BTV 10_S10_654R. Amplified targets were sequenced using BTV 10_S 10_ 238F. (C; SEQ ID NO: 23). Reassortant with BTV-10 segment 10 introduced. (D; SEQ ID NO: 24). Reassortant with HaeII site-containing BTV-10 segment 10 introduced. Arrow indicates the introduced point mutation.

FIG. 5 shows double reassortant progeny genomes containing the plasmid-derived BTV-10 segments 2 and 5. (A). Genomic dsRNA from BTV recovered from the co-transfection of BSR cells with the BTV-10 segment 5 T7 transcript, the BTV-10 segment 2 T7 transcript, and core-derived BTV-1 transcripts. Genomic dsRNA from progeny plaques run on a 9% non-denaturing polyacrylamide gel. Lanes 1-3, viral dsRNA from three plaque purified reassortants. Arrows indicate the slower migrating BTV-10 segment 2 and segment 5. BTV-1 dsRNA and BTV-10 dsRNA marker lanes indicated. (B and C). Restriction digest analysis of segment 2 and segment 5 RT-PCR products. Target regions from segment 2 and segment 5 were RT-PCR amplified from genomic dsRNA, digested with restriction enzymes specific to the BTV-10 segment and separated on 1.5% agarose gels. (B). SacI digestion of segment 2 RT-PCR products. SacI has specificity for segment 2 of serotype 10, with two sites in the target sequence. RT-PCR products amplified from genomic dsRNA using segment 2 primers BTV10_L2_727F and BTV10_L2_1523R. U=undigested RT-PCR product, D=SacI digested RT-PCR product. Note primer pair does not amplify BTV-1 segment 2 due to the low homology of this segment among different serotypes. Lanes 1, BTV-1, lanes 2, BTV-10, lanes 3, reassortant with BTV-10 segments 2 and 5 introduced. StyI-digested phage λ DNA marker sizes in by indicated on left. Size of RT-PCR product and digest fragments indicated on right in bp. (C). DraI digestion of segment 5 RT-PCR products. DraI has specificity for segment 5 of serotype 10, with two sites present in the target sequence. RT-PCR products amplified from genomic dsRNA using segment 5 primers BTV10_M5_724F and BTV10_M5_1590R. U=undigested RT-PCR product, D=DraI digested RT-PCR product. Templates in RT-PCR reactions are as indicated for panel B. Size of RT-PCR product and digest fragments indicated on right in bp.

FIG. 7 shows the recovery of infectious BTV by transfection with ten T7 transcripts. (A). Transfected BSR monolayers overlaid with agarose. Well 1, BSR transfected with 4 μg BTV-1 T7 transcripts, well 2, BSR not transfected. Monolayers were fixed and stained with crystal violet at 5 days after transfection. (B). Genomic dsRNA run on a 9% non-denaturing polyacrylamide gel, extracted from BTV recovered from the transfection of BSR monolayers as described in panel A. Lane 1, BTV-1 stock virus, lanes 2 and 3, BTV-1 from separate plaques derived from transfection with T7 transcripts.

FIG. 8 shows the recovery of infectious BTV containing a marker mutation using ten T7 transcripts. (A). Transfected BSR monolayers overlaid with agarose. Well 1, BSR transfected with 3 μg BTV-1 T7 transcripts including a segment 8 transcript with an introduced BglII site, well 2, BSR not transfected. Monolayers were fixed and stained with crystal violet at 5 days after transfection. (B). Genomic dsRNA run on a 9% non-denaturing polyacrylamide gel, extracted from BTV recovered from the transfection of BSR monolayers as described in panel A. Lane 1, BTV-1 stock virus, lanes 2 and 3, BTV-1 from separate plaques derived from transfection with T7 transcripts.

FIG. 13 shows that the BTV1 delta VP6 has genome segment 9 replaced by a smaller genome segment. (A) Genomic dsRNA run on 9% non-denaturing polyacrylamide gels. Arrow indicates the new genome segment present in BTV1 delta VP6. Genome segment numbers indicated on right hand side. (B) RT-PCR products generated from genomic dsRNA derived from the indicated sources using EcoT7_S9_F and EcoBsmB_S9_R primers, and resolved on a 1% agarose gel. Sizes of DNA markers indicated in base pairs.

FIG. 14 shows that the BTV1 delta VP6 does not produce infectious progeny in infected BSR or C6/36 Cells. The production of infectious progeny was assayed at intervals over 72 hours by plaque assay on the complementing BSR VP6 cell line. Plot of the replication of BTV1 delta VP6 and wildtype BTV-1 on BSR cells (A), or C6/36 cells (B).

FIG. 16 shows that BTV1 S10GFP has a larger genome segment replacing the S10 segment. (A) Genomic dsRNA run on 11% non-denaturing polyacrylamide gels. Arrow indicates the new genome segment present in BTV1 S10GFP. Genome segment numbers indicated on right hand side. (B) RT-PCR products generated from genomic dsRNA derived from the indicated sources, and resolved on a 1% agarose gel. Sizes of DNA markers indicated in base pairs.

FIG. 17 shows the expression of a marker antigen from the BTV genome. C6/36 were infected with the BTV1 S10 GFP (A and B), or mock infected (C and D). At 5 days post-infection the cells were fixed in 4% w/v paraformaldehyde and their appearance recorded under phase contrast (A and C), or UV light (Band D).

DETAILED DESCRIPTION

EXAMPLES

Figure 2:
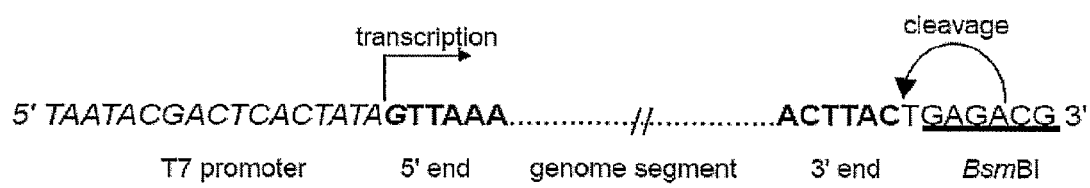
FIG. 2 is a schematic drawing of T7 BTV plasmid clones. T7 plasmids contain the full length BTV genome segment flanked by a T7 promoter and a BsmBI, BsaI or BpiI restriction enzyme site which defines the BTV 3' end sequence during transcription. The sequences at the 5' (SEQ ID NO: 19) and 3' (SEQ ID NO: 20) ends of the BTV genome segment and the flanking sequences are indicated; T7 promoter (italicized), the conserved BTV genome segment 5' and 3' end sequences (bold), and the BsmBI site (underlined).

The new approach to vaccine design uses a novel reverse genetics method developed by the inventors. It builds on the discovery that bluetongue virus transcripts are infectious by transfection [1], and allows the replacement of targeted segments with cloned versions of the viral genes. The method uses the novel approach of transfecting virus permissive cells with BTV transcripts mixed with bacteriophage T7 in vitro transcripts of BTV segments derived from cloned genes. Virus containing the replacing genome segment is isolated by screening virus plaques. This new method of reverse genetics differs from the existing reverse genetics technologies used in the Reoviridae family: 1) The helper virus-dependent method of Roner et al. [3] successfully applied to mammalian orthoreoviruses. Viral transcripts and viral dsRNA are mixed with T7 in vitro transcripts and rescued using a helper virus infection; 2) The helper virus-dependent method of Komoto et al. [2] used to alter a capsid protein of rotavirus. The T7 transcript is generated in the cell using the vaccinia T7 RNA polymerase system, and rescued using a helper virus strain; and 3) The plasmid-based method of Kobayashi et al. [4] used to make mutation in mammalian orthoreovirus genes. All the viral genome segments are generated in the cell using the vaccinia T7 RNA polymerase system.

The new approach uses reverse-genetics to produce vaccine strains which contain the immunologically relevant bluetongue proteins (VP2 and VP5) from the serotype of interest with a universal background of the other viral proteins. This is coupled with inactivation of one or more essential viral genes through extensive mutation, by reverse genetics, which are provided by a complementing cell line. The virus produced can only be grown in the complementing cell line and is capable of only a single round of replication in other cells such as those of a vaccinated animal. The targeting of one or more BTV enzymatic proteins (polymerase, helicase and capping proteins) or alternatively BTV non-structural viral proteins for inactivation by reverse-genetics will allow the use of a DIVA strategy for surveillance purposes. The new approach also eliminates the problem of under-attenuation and reduces the time delay from identification of a new serotype to production of a vaccine strain, associated with attenuating new strains. The probability of reversion to virulence is greatly reduced through the use of extensive mutations in the viral genes targeted. The probability of reassortment with wild-type virus producing an infectious virus is also much reduced by the fact that the vaccine strain only undergoes a single replication cycle in the vaccinated animal. The new approach also avoids the need to confirm the inactivation of vaccine batches associated with inactivated vaccines.

The present technique has been used to produce a DISC (disabled infectious single cycle) vaccine for BTV, wherein an essential gene (VP6) was manipulated through the reverse genetics system and its function was destroyed through a large deletion. The VP6 deletion mutant (BTV1 delta VP6) was recovered using the reverse genetics technique in combination with a complementing cell line which supplied the VP6 protein in trans. Characterisation of the growth properties of BTV1 delta VP6 showed that it has the necessary characteristics for a BTV DISC vaccine i.e., i) expression of viral proteins in non-complementing mammalian cells; ii) no detectable infectious virus generated in non-complementing mammalian or insect cell lines; and iii) robust replication in the complementing VP6 cell line. Additionally, the ability to create a virus express a foreign protein/peptide has been demonstrated using an NS3 complementing cell line in combination with a BTV which has the enhanced green fluorescent protein (eGFP) inserted in the centre of the NS3 gene. This allows the production of vaccine strains containing an immunological marker which can be detected in vaccinated animals to distinguish them from infected animals, i.e., the DIVA concept (distinguishing infected and vaccinated animals).

Material and Methods

Cell Lines and Virus. BSR cells (a clone of BHK-21) were cultured in Dulbecco's modified Eagle's medium (DMEM) supplemented with 5% v/v foetal bovine serum (FBS), at 35° C. in 5% $CO_2$.

BTV stocks were generated by infecting BSR cells at a multiplicity of infection (MOI) of 0.1 and harvesting the medium at 3-4 days post-infection. Viral stocks were stored at 4° C.

Purification of Bluetongue Virus Cores. BSR cultures were infected with BTV at an MOI of 0.02-0.1. Transcriptionally active BTV-1 cores were purified as previously described and stored at 4° C. [1].

Synthesis and Purification of Bluetongue Virus mRNA In Vitro. BTV cores were incubated at 40 μg/ml at 30° C. for 5-6 hours in BTV core transcription buffer (100 mM Tris HCl pH8.0, 4 mM ATP, 2 mM GTP, 2 mM CTP, 2 mM UTP, 500 μM S-adenosylmethionine, 6 mM DTT, 9 mM $MgCl_2$, 0.5 U/μl RNasin® Plus [Promega]).

BTV core-derived mRNAs were purified using the previously described method, and stored at −80° C. [1].

RT-PCR Amplification of BTV-1 Genome Segments. CDNA copies of each BTV-1 genome segment were amplified from viral dsRNA in a sequence independent manner using the FLAC method [18]. Briefly, the hairpin anchor primer was ligated to viral dsRNA as described, followed by cDNA synthesis from gel purified genome segments with SuperScript™ III (Invitrogen) at 10U/μl, 55° C. for 1 hour. PCR amplification was performed using 5' phosphorylated FLAC 2 primer (5' GAGTTAATTAAGCGGCCGCAGTT-TAGAATCCTCAGAGGTC3'; SEQ ID NO: 1) with KOD Hot Start DNA Polymerase (Novagen). PacI and NotI sites are in bold type.

T7 Plasmid Clones Used for the Synthesis of BTV Transcripts. CDNA plasmid clones were constructed for BTV-10 genome segment 10 (pNS3BsmBI), segment 5 (pVP5BsmBI), and segment 2 (pVP2BsmBI), and for all ten segments of the BTV-1 genome. A mutant version of the BTV-10 segment 10 clone, containing an introduced HaeII site (pNS3Hae), and a mutant version of the BTV-1 segment 8 clone, containing an introduced BglII site (pBTV1S8Bgl) were also constructed. The functional cassette in each plasmid clone contained a T7 promoter and a BsmBI, BsaI, or BpiI site, with the BTV genome segment located between these elements. The BTV genome segment in each clone was positioned relative to the other two sequence elements such that the T7 transcript derived from plasmid digested with BsmBI, BsaI, or BpiI was predicted to have exactly the same sequence as the mRNA strand of the corresponding BTV genome segment (FIG. 2).

Synthesis of BTV Transcripts from cDNA Plasmid Clones. T7 plasmid clones were digested with BsmBI, BsaI, or BpiI then extracted once with phenol/chloroform and once with chloroform. Each digested plasmid was precipitated with isopropanol in the presence of 0.15M sodium acetate. DNA pellets were washed twice in 70% (v/v) ethanol and dissolved at 1 μg/μl in 10 mM Tris HCl pH8.0. Transcripts with a 5' cap analogue were generated from the digested T7 plasmid clones using the mMESSAGE mMACHINE® T7 ULTRA Kit (Ambion), using a 4:1 ratio of anti-reverse cap analogue to rGTP. T7 BTV transcripts were extracted once with phenol/chloroform followed by one extraction with chloroform. Unincorporated rNTPs were removed by size fractionation using Microspin™ G-25 columns (GE Healthcare) according to the manufacturer's instructions. The T7 BTV transcripts were precipitated with an equal volume of isopropanol in the presence of 0.15M sodium acetate. RNA pellets were washed twice in 70% (v/v) ethanol and dissolved in sterile diethylpyrocarbonate (DEPC) treated water, and stored at −80° C.

Denaturing Agarose Gel Electrophoresis. Purified BTV ssRNA was analyzed by electrophoresis on 1% agarose in MOPS (morpholinepropanesulfonic acid) electrophoresis buffer in the presence of formaldehyde, using standard techniques [19].

Transfection of Cultured Cells to Recover Bluetongue Virus with One or Two cDNA-Derived Genome Segments. BTV mRNAs derived from transcribing cores were mixed with one or more T7 BTV transcripts in Opti-MEM®I, in the presence of 0.1 U/μl RNasin® Plus (Promega). The RNA mixture was incubated at 20° C. for 30 minutes before mixing with Lipofectamine™ 2000 Reagent (Invitrogen) [see below]. Confluent BSR monolayers in 6 well plates were transfected with 1.5 μg BTV mRNA mixed with 0.75 μg of each T7 BTV transcript using Lipofectamine™ 2000 Reagent according to the manufacturer's instructions. At 4 hours post-transfection the culture medium was replaced with a 6 ml overlay consisting of minimal essential medium (MEM), 2% FBS, 1.5% w/v agarose type VII (Sigma). Assays were incubated at 35° C., 5% $CO_2$ for 72-96 hours to allow plaques to appear.

Transfection of Cultured Cells to Recover Bluetongue Virus Entirely from cDNA-Derived Genome Segments. 300-400 ng of each T7 BTV transcript were mixed, as described above, to produce a complete genome set of T7 BTV transcripts. Transfection of BSR monolayers was performed as described above.

Preparation of dsRNA from Transfection-Derived BTV Plaques. Each plaque was picked into 500 μl Dulbecco's modified Eagle's medium (DMEM), 5% FBS, and 200 μl was used to infect $1.5 \times 10^6$ BSR. Infected cells were incubated at 35° C. in 5% $CO_2$ for 72-96 hours to allow amplification of the BTV. Viral dsRNA was purified from infected BSR cells as previously described [1].

Screening Transfection-Derived BTV Plaques for Reassortants Containing the Introduced Genome Segments. Where the genome segment being introduced migrated at a different rate on polyacrylamide gels, screening was done by electrophoresis of the dsRNA on 9% polyacrylamide gels in Tris/glycine buffer (pH8.3). Gels were post-stained for 30 minutes with ethidium bromide. Where screening was not possible on the basis of the migration rate, RT-PCR (reverse transcription polymerase chain reaction) followed by restriction endonuclease digestion was used to discriminate between reassortants and wild-type BTV. CDNA was synthesized from 100 ng heat denatured viral dsRNA with SuperScript™ III (Invitrogen) using forward and reverse primers flanking the target region, at 55° C. for 1 hour. The target region was PCR amplified using Taq DNA polymerase with the same forward and reverse primers and digested with restriction endonucleases. Products were resolved by electrophoresis in agarose gels containing ethidium bromide, in Tris-borate-EDTA buffer. Sequence analysis of RT-PCR products was done using dye terminators on ABI 3730XL sequencing machines using the Value Read service of MWG Biotech [20].

Construction of pNS3Hae and pBTV1S8Bgl. PNS3BsmBI was altered to contain an additional HaeII site by site-directed mutagenesis using primers S10_mt_Hae_409F and S10_mt_Hae_409R by the method of Weiner et al [17]. Similarly the wildtype BTV-1 S8 clone was altered to introduce a BglII site using primers 5'BTV1_S8_BglII and 3'BTV1_S8_BglII. Clones were screened for the presence of the introduced site by HaeII or BglII digestion, and the expression cassette sequenced to identify clones containing no adventitious mutations using the Value Read service of MWG Biotech.

Primers. Mutagenic primers used to generate pNS3Hae from pNS3BsmBI:
S10-mt_Hae_409F
(5'CTACTAGTGGCTGCTGTGGTAGCGCTGCTGACATCAGTTTG3'; SEQ ID NO: 2)
and S10-mt_Hae_409R
(5'CAAACTGATGTCAGCAGCGCTACCACAGCAGCCACTAGTAG3'; SEQ ID NO: 3).
Mutagenic primers used to generate pBTV1S8Bgl from the wildtype BTV-1 S8 clone:

5'BTV1_S8_BglII
(5'GATTTACCAGGTGTGATGAGATCTAACTACGATGTTCGTGAAC3'; SEQ ID NO: 4)
and 3'BTV1_S8_BglII
(5'CGAACATCGTAGTTAGATCTCATCACACCTGGTAAATCGGGC3'; SEQ ID NO: 5).
The mutagenic bases are underlined and the restriction sites are in bold type.

Primers for the RT-PCR amplification and sequencing of BTV-10 segment 10:
BTV10_S10_238F
(5'GGAGAAGGCTGCATTCGCATCG3'; SEQ ID NO: 6),

BTV10_S10_654R
(5'CTCATCCTCACTGCGTCATTATATGATTGTTTTTTCATCACTTC3'; SEQ ID NO: 7),

BTV10_S10_259F
(5'GGAGAAGGCTGCATTCGCATCG3'; SEQ ID NO: 6),

BTV10_S10_611R
(5'CTCATCCTCACTGCGTCATTATATGATTGTTTTTTCATCACTTC3'; SEQ ID NO: 7).

Primers for RT-PCR amplification from BTV-10 segment 5:
BTV10_M5_724F
(5'ATGACAGCAGACGTGCTAGAGGCGGCATC3'; SEQ ID NO: 8)
and

BTV10_M5_1590R
(5'GCGTTCAAGCATTTCGTAAGAAGAG3'; SEQ ID NO: 9).

Primers for RT-PCR amplification from BTV-10 segment 2:
BTV10_L2_727F
(5'CCGTACGAACGATTTATATCCAGC3'; SEQ ID NO: 10)
and

BTV10_L2_1523R
(5'TACTAATTCAGAACGCGCGCC3'; SEQ ID NO: 11).

Primers for RT-PCR amplification of BTV-1 segment 8:
NS2_Bam_T7F
(5'CGGGATCCTAATACGACTCACTATAGTTAAAAAATCCTTGAGTCA3'; SEQ ID NO: 12)
and NS2_Bam_R
(5'CATGGGATCCGGACCGTCTCCGTAAGTGTAAAATCCCC3'; SEQ ID NO: 13).

Primer for sequencing BTV-1 segment 8:
BTV1_S8_627R
(5'CAGCTTCTCCAATCTGCTGG3'; SEQ ID NO: 14).

Construction of stable cell lines expressing the BTV VP6 or NS3 protein. The coding regions for BTV-10 VP6 and BTV-1 NS3 were amplified by PCR and cloned into the puromycin selectable plasmid pCAGGS/MCS-PM1 [29], to obtain pCAGGNP6 and pCAGG/NS3, respectively. BSR cells were transfected with pCAGGNP6 or pCAGG/NS3 using Lipofectamine™ 2000 Reagent (Invitrogen) and 48 hours post-transfection were trypsinized and selected with puromycin at 7.5 μg/ml. Isolated resistant colonies were cultured and the expression of the VP6 or NS3 protein was tested by immunoblotting using an appropriate antibody. The VP6 and NS3 expressing lines were termed BSR VP6 and BSR NS3.

Figure 10:
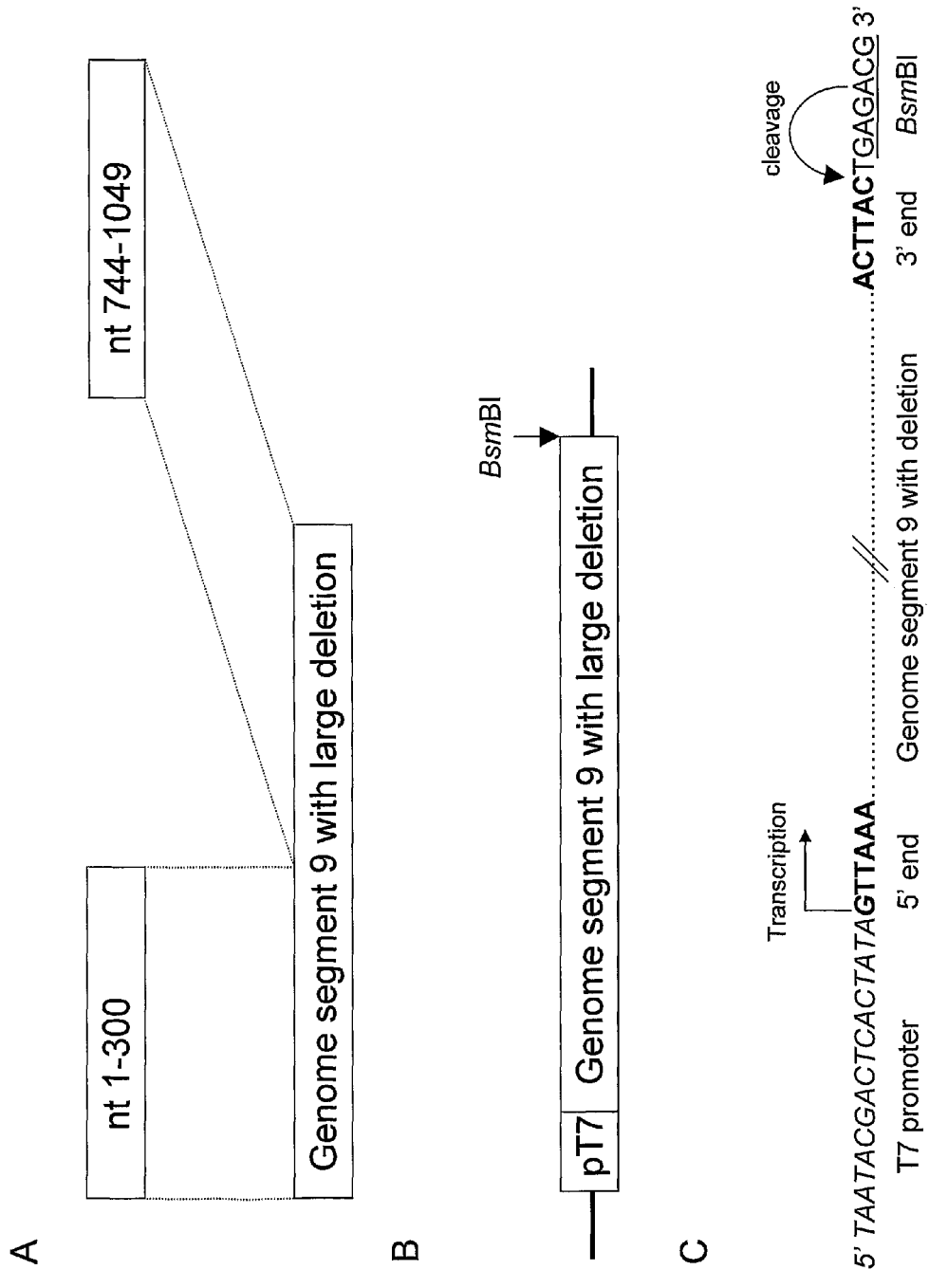
FIG. 10 shows the pBTV1 S9delta Clone used in the Generation of BTV1 delta VP6. (A) The nucleotide co-ordinates of genome segment 9 retained in the pBTV1 S9delta clone. (B) pBTV1 S9delta contains the modified BTV genome segment 9 flanked by a T7 promoter and a BsmBI restriction enzyme site which defines the BTV 3' end sequence during transcription. (C) The sequences at the 5' (SEQ ID NO: 19) and 3' (SEQ ID NO: 20) ends of the BTV genome segment and the flanking sequences are indicated: T7 promoter (italicized); the conserved BTV genome segment 5' and 3' end sequences (bold); and the BsmBI site (underlined).

The recovery of BTV, using the complementing BSR VP6 or BSR NS3 cell line. A BTV-1 segment 9 clone with an out of frame deletion of nucleotides 301-743 (out of 1049 nt) was constructed, pBTV1 S9delta (FIG. 10). The corresponding mutant virus, BTV1 delta VP6, was recovered, using the BSR VP6 cell line in the place of wildtype BSR cells during transfection. Similarly, a BTV-1 segment 10 clone with the enhanced green fluorescent protein (eGFP) inserted in the centre of the NS3 gene was constructed, pBTV1 S10GFP. The corresponding GFP expressing virus, BTV1 S10GFP, was recovered, using the BSR NS3 cell line during transfection.

Passaging of BTV1 delta VP6 and BTV1 S10GFP. BTV1 delta VP6 was passaged on the BSR VP6 cell line, and the titre determined by plaque assay also using the BSR VP6 cell line. BTV1 S10 GFP was passaged on the BSR NS3 cell line, and the titre determined by plaque assay also using the BSR NS3 cell line.

Multi Step Growth Curves of BTV1 delta VP6. BSR or C6/36 cells were infected at an MOI of 0.5 in twelve well dishes in 250 μl of DMEM or L15 medium, respectively. Wells were washed three times in 1 ml PBS and incubated under standard growth conditions in 1 ml of growth medium.

Wells were harvested at time intervals and the total virus determined by plaque assay titration on the BSR VP6 complementing cell line.

```
Primers.
EcoT7_S9_F
(5'CTAGGAATTCTAATACGACTCACTATAGTTAAAAAATCGCATATGTC

AGCTGC3'; SEQ ID NO: 15).

EcoBsmB_S9_R
(5'CAGTGAATTCGTCTCCGTAAGTGTAAAATCGCCCTACG3';
SEQ ID NO: 16)

BTV1S10T7EcoRI
(5'CGGAATTCTAATACGACTCACTATAGTTAAAAAGTGTCGCTGCCATG

CTA3'; SEQ ID NO: 17)

NS3BsmBi rev
(5'GTAAGTGTGTAGTATCGCGCACC3'; SEQ ID NO: 18)
```

Results

Figure 1:
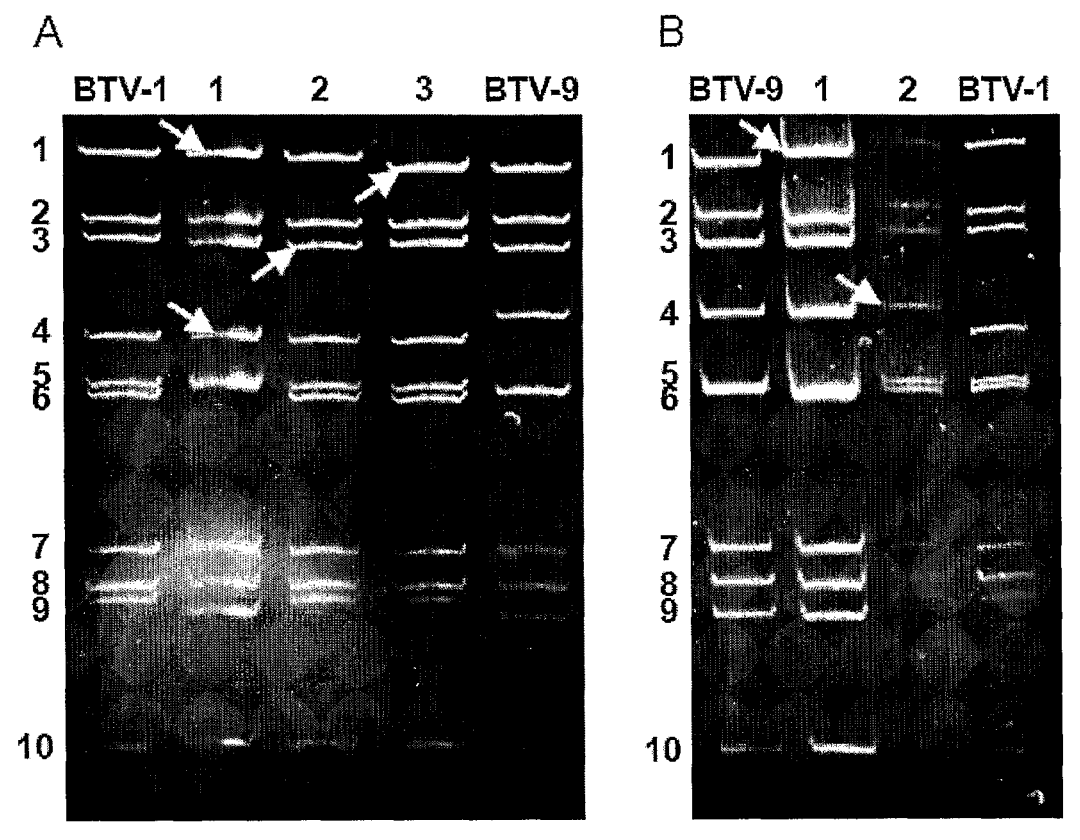

Reassortment of Genome Segments by Co-transfection with BTV mRNA from Two Serotypes. The recovery of infectious BTV from core-derived transcripts through the transfection of permissive cells has been demonstrated [1]. With the aim of producing a reverse genetics system for BTV, the introduction of genome segments from one BTV serotype into another was investigated as an intermediate step, prior to the introduction of cDNA-derived genome segments. Infectious core-derived transcripts were prepared from BTV-1 and BTV-9 as previously described [1]. The transcripts from the two serotypes were either generated simultaneously in the same transcription reaction or prepared separately and then mixed. Confluent BSR monolayers were transfected with the transcript mixtures and virus was amplified from the resulting plaques. The dsRNA was purified from each amplified plaque and the origin of genome segments was determined by electrophoresis on non-denaturing PAGE gels, which allow the discrimination of some genome segments from different isolates. When co-synthesized transcripts from BTV-1 and BTV-9 were used, progeny viruses were generated which had genome segments from both parental sources of transcripts [reassortants] (FIG. 1A). Lane 1 contains a reassortant which has segment 1 and segment 4 of BTV-1 in a genetic background of segments which migrate as BTV-9. Similarly, lane 2 contains a reassortant with the segment 3 of BTV-9 in a BTV-1 genetic background, and lane 3 contains a reassortant with segment 1 of BTV-9 in a BTV-1 genetic background. When BTV-1 and BTV-9 transcripts were prepared separately and mixed prior to transfection, reassortant progeny viruses were also generated, indicating that co-synthesis of transcripts is not necessary for reassortment to occur (FIG. 1B). These data demonstrated that co-transfection with a mixture of viral transcripts is a viable strategy for the introduction of genome segments from a separate source into the BTV genome.

The Introduction of a BTV Segment Derived from a cDNA Clone into the BTV-1 Genome. The targeted replacement of a genome segment with a T7 transcript derived from a cDNA clone was subsequently investigated as a model for the introduction of cloned sequences into the BTV genome. The introduction of the BTV-10 segment 10 T7 transcript into the genome of BTV-1 was chosen to allow the rapid screening of plaques based on the faster migration rate of segment 10 of BTV-10 compared to BTV-1, on PAGE gels. The BTV-10 segment 10 T7 transcript was produced from pNS3BsmBI which has a T7 promoter to generate the correct 5' end sequence and a BsmBI site to generate the correct 3' end sequence (FIG. 2). BTV-1 transcripts produced from transcribing cores were mixed with the BTV-10 segment 10 T7 transcript and used to transfect confluent BSR monolayers. A 5:1 molar ratio of T7 transcript to the corresponding core-derived mRNA was found to be best and was used in all experiments. Increasing the ratio of T7 transcript to BTV1 transcripts reduced the total number of plaques recovered (data not shown). Typically ~50 plaques were recovered from each well following the transfection of a six well dish with 1.5 µg core-derived transcripts plus 0.75 µg T7 transcript. Virus was amplified from these plaques and the dsRNA purified. The origin of genome segment 10 was initially determined by electrophoresis of the dsRNA on PAGE gels. DsRNA genome profiles containing the faster migrating segment 10 from BTV-10 were obtained with a sufficiently high frequency (15-80%) to make screening of plaques a viable option (FIG. 3A). The identity of segment 10 was confirmed using RT-PCR followed by sequencing of a region showing variability between type 1 and type 10 (FIGS. 3B, C and D). These data demonstrated the recovery of the plasmid-derived BTV-10 segment 10 into the genome of viable BTV-1.

BTV naturally produces reassorted progeny genomes when a cell is infected with two different strains [21]. To abolish the possibility of natural reassortment between two viruses being the origin of the segment 10 reassortants, a BTV-10 segment 10 clone containing an introduced silent HaeII site (pNS3Hae) as a marker was made by the site directed mutagenesis of pNS3BsmBI. BSR monolayers were transfected with a mixture of BTV-1 core-derived mRNAs and the BTV-10 segment 10 T7 transcript containing the introduced mutation, derived from pNS3Hae. The recovery of virus containing this mutant BTV-10 segment 10 sequence was initially screened for by its increased migration rate on PAGE gels (FIG. 4A). The introduction of the HaeII site into segment 10 of the BTV genome was confirmed by RT-PCR of dsRNA from plaque purified virus, followed by HaeII digestion (FIG. 4B), and by sequencing of the RT-PCR product (FIGS. 4C and D). Segment 10 was determined to be the same as the segment encoded in pNS3Hae throughout its length, by sequencing a full-length RT-PCR product (data not shown).

The Simultaneous Introduction of two BTV-10 Segments Derived from cDNA Clones into the BTV-1 Genome. To assess this possibility of simultaneously altering two genome segments the introduction of the outer capsid protein encoding segments (segments 2 and 5) from BTV-10 into a background of BTV-1 genome segments was investigated. Replacement of these genome segments with the segments from another serotype would enable the serotype of the virus to be altered. T7 transcripts derived from segments 2 and 5 of BTV-10 were prepared from pVP2BsmBI and pVP5BsmBI respectively and mixed with BTV-1 core-derived mRNAs at a 5:1 ratio of each T7 transcript to the corresponding core-derived transcript. Confluent BSR cell monolayers were transfected with the RNA mixture, and dsRNA prepared from the recovered plaques. The origin of segments 2 and 5 were initially assessed by their migration rate on PAGE gels (FIG. 5A). Both segments 2 and 5 from BTV-10 were recovered together at high frequency (20-80%). The identity of the segments was confirmed by RT-PCR followed by restriction digestion (FIGS. 5B and C). The complete sequence of segment 2 and segment 5 was determined to be that of BTV-10 by RT-PCR amplification and sequencing (data not shown). No progeny (0 out of 19 plaques from three independent experiments) were recovered which contained only segment 2 or only segment 5 from BTV-10, suggesting that viruses containing segment 2 from one parent and segment 5 from the other parent are either of reduced viability, or are generated at a lower frequency than the double reassortants. This phenomenon was further supported when the introduction of segment 2 or segment 5 from BTV-10 into BTV-1 was attempted singly and no reassortant progeny were recovered (data not shown).

Figure 6:
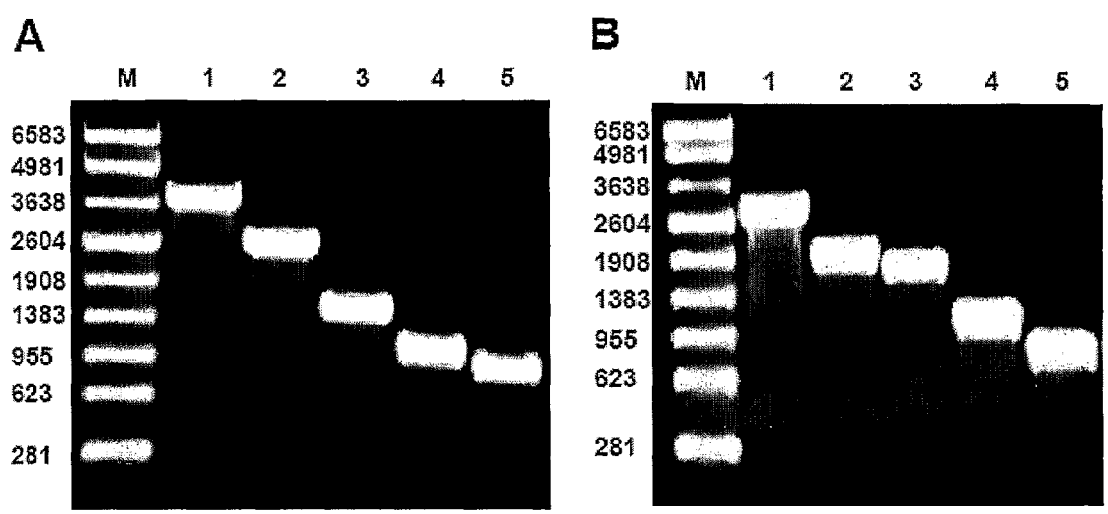
FIG. 6 shows T7 transcripts of BTV-1 genome segments. Denaturing 1% agarose gel electrophoresis of BTV-1 T7 transcripts generated from restriction endonuclease digested clones. M=1 μg ssRNA markers (Promega), with sizes in nt indicated. (A). Lane 1—segment 1, lane 2—segment 3, lane 3—segment 5, lane 4—segment 7, lane 5—segment 9. (B). Lane 1—segment 2, lane 2—segment 4, lane 3—segment 6, lane 4—segment 8, lane 5—segment 10.

The Recovery of BTV Entirely from T7 Transcripts. While the above method is a viable reverse genetics system which allows the manipulation of BTV genome segments the screening of reassortant plaques from wildtype plaques could hinder the recovery of slow growing mutants. The ideal reverse genetics system would permit the assembly of infectious virus entirely from T7 transcripts. To maximise the probability of having a viable clone for every genome segment RT-PCR amplification of each genome segment was performed with dsRNA of BTV-1, using the sequence-independent FLAC method developed for dsRNA templates [18]. Each RT-PCR product was cloned into pUC19 [22] and the complete sequence of each clone was compared with the complete sequence of each RT-PCR product in order to determine whether a representative molecule had been cloned in each case (data not shown). Alternative clones were sequenced when coding changes or any differences within 200 nt of the ends of the cloned genome segment were present. Once a complete set of ten clones was obtained each genome segment was PCR amplified using the high fidelity IOD Hot Start DNA Polymerase (Novagen) to introduce a T7 promoter directly upstream of the genome segment and a restriction enzyme site directly downstream (FIG. 2). These functional cassettes were also cloned in pUC19. T7 transcripts synthesized using the restriction digested plasmid clones were determined to be of the expected size when resolved on 1% denaturing agarose gels (FIGS. 6A and B).

T7 transcripts made from restriction digested plasmids were mixed in equal ratio by weight, and 3-4 µg in total used to transfect confluent BSR monolayers. Transfected monolayers were overlaid with agarose and plaques appeared at 3-6 days post-transfection (FIG. 7A). DsRNA from amplified plaques was compared with BTV-1 stock virus on PAGE gels, and found to be indistinguishable, confirming that BTV-1 had been recovered (FIG. 7B). To substantiate further that BTV could be derived from T7 transcripts a mutant of the BTV-1 segment 8 T7 clone was made which contained an introduced silent BglII site, pBTV1S8Bgl. Plaques were recovered from transfections with a complete set of T7 transcripts where the segment 8 BglII marker transcript replaced the wildtype S8 transcript (FIG. 8A). DsRNA from amplified plaques was found to be indistinguishable when compared with BTV-1 stock virus on PAGE gels (FIG. 8B). Plaques were amplified by infection of BSR cells and the S8 segment amplified by RT-PCR using primers NS2_Bam_R and NS2_Bam_T7—F. Digestion of the RT-PCR product demonstrated that a BglII site had been introduced (FIG. 9A). The RT-PCR products were sequenced using the BTV1—S8_627R primer confirming the introduction of the marker sequence (FIG. 9B). These data demonstrate that it is possible to recover BTV from a complete genomic set of T7 transcripts, and introduce viable mutations using this system.

Recovery of the BTV1 delta VP6 Virus. To generate a DISC vaccine strain a large out of frame deletion in the essential protein VP6 was made in a wildtype segment 9 clone to generate pBTV1 S9delta (FIG. 10). A complete genomic set of in vitro synthesised T7 transcripts was made as previously described, but containing the deleted segment 9 transcript instead of the wildtype segment 9 transcript. The corresponding mutant virus, BTV1 delta VP6, was recovered, using the BSR VP6 cell line in the place of wildtype BSR cells during transfection. Cytopathic effect (CPE) indistinguishable from BTV CPE was visible in transfected wells by 5 days post-transfection, indicating the recovery of infectious virus (data not shown).

Figure 11:
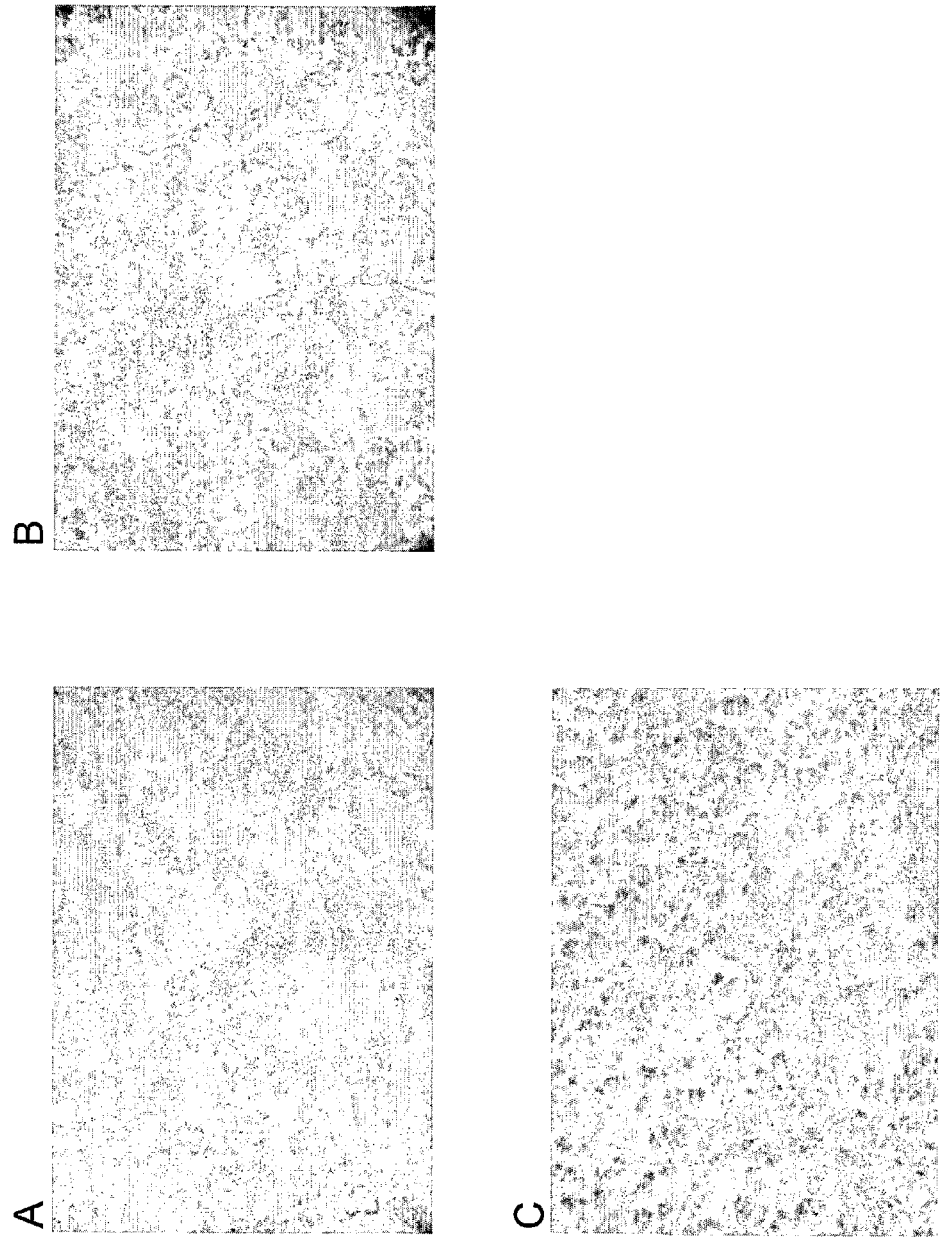
FIG. 11 shows that BTV1 delta VP6 produces CPE in the complementing BSR VP6 cell line. Monolayers were infected at an MOI of 0.1 and the appearance recorded at 48 hours post-infection using phase contrast microscopy. (A) BSR VP6 cells infected with BTV1 delta VP6. (B) Wildtype BSR cells infected with wildtype BTV-1. (C) Mock infected BSR cells.

BTV1 delta VP6 replicates in the BSR VP6 cell line. To determine whether the BTV1 delta VP6 virus replicates robustly in the BSR VP6 cell line it was compared to wildtype BTV-1 replication in wildtype BSR cells. CPE produced by the infection of the BSR VP6 cell line with BTV1 delta VP6 was equivalent to that produced when wildtype BTV-1 was used to infect wildtype BSR cells, indicating that there is no gross defect in the replication of BTV1 delta VP6 (see FIG. 11). The plaque-forming potential of BTV1 delta VP6 was assessed using the BSR VP6 cell line (see FIG. 12). The BSR VP6 cell line was found to complement the growth of BTV1 delta VP6 such that plaques of a normal appearance were produced, enabling the normal titration of BTV1 delta VP6. BTV1 delta VP6 virus could be grown to comparable titres to wildtype BTV-1 (over $10^7$ infectious units/ml) using the BSR VP6 cell line. These data demonstrate that the BTV1 delta VP6 virus replicates efficiently in the complementing BSR VP6 cell line.

Characterisation of genome segment 9 of BTV1 deltaVP6. BTV1 delta VP6 was propagated on the BSR VP6 cell line, and the viral double-stranded RNA extracted and purified as previously described. The BTV1 delta VP6 genome lacks the wildtype S9 segment and contains a smaller genome segment, corresponding to the replacement of the wildtype S9 segment with the deleted S9 segment (FIG. 13A). The S9 segment from BTV1 delta VP6 was amplified by RT-PCR using primers annealing at the ends of the S9 segment (EcoT7_S9_F and EcoBsmB_S9—R), generating the expected product of 650 nt (FIG. 13B), and sequenced with the same primers. The observed sequence of the amplified genome segment was identical to that in the pBTV1 S9delta (data not shown), demonstrating that the virus recovered was constructed correctly.

Characterisation of the growth of BTV1 delta VP6 on non-complementing cell lines. An important characteristic of a DISC vaccine strain is that it should be unable to complete a replication cycle in the host organism. To evaluate whether BTV1 delta VP6 is defective, the mammalian line BSR (a BHK-21 sub clone), and the insect cell line C6/36, lines in which BTV replicates efficiently, were used as proxies for the mammalian and insect hosts. Both cell lines were infected with BTV1 delta VP6, and the total virus produced monitored by plaque assay using the BSR VP6 complementing cell line, over 72 hours. BTV1 delta VP6 did not replicate in either cell line, whereas wildtype BTV-1 showed efficient replication in both lines (FIGS. 14A and B). This data demonstrates that the disruption of the VP6 gene has rendered the virus incapable of replicating when the VP6 protein is not supplied by the complementing cell line.

Figure 15:
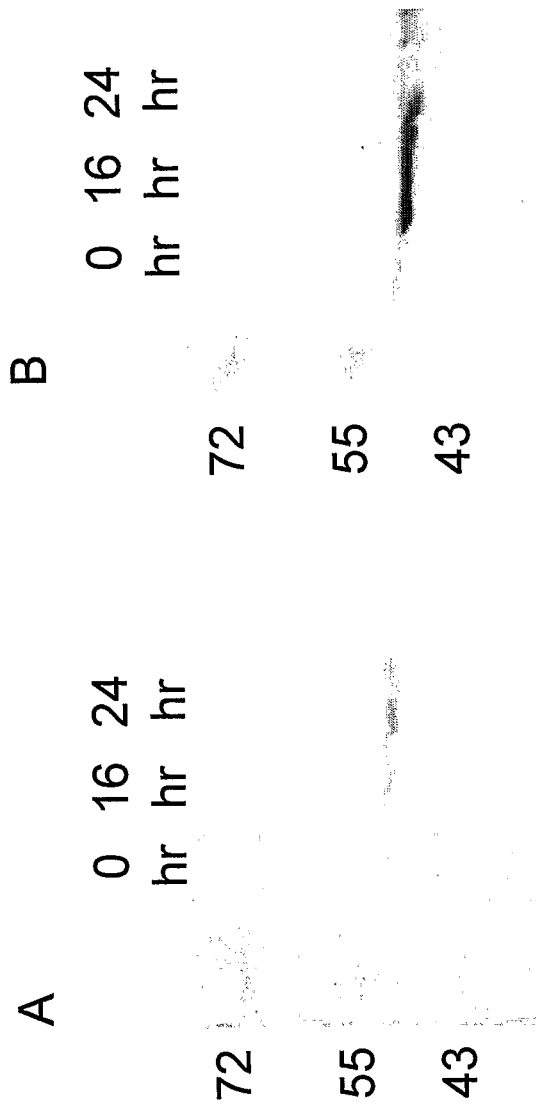
FIG. 15 shows that BTV1 delta VP6 expresses viral protein in non-complementing BSR cells. BSR cells were infected at an MOI of 3, and harvested at the indicated number of hours post-infection. NS2 expression was detected by SDS PAGE followed by immunoblotting with NS2-specific antiserum. (A) BSR infected with BTV1 delta VP6, (B) BSR infected with wildtype BTV-1. Sizes of pre-strained protein molecular weight markers indicated in kDa.

BTV1 delta VP6 expresses viral proteins in non-complementing BSR cells. Any DISC vaccine must express virus proteins in the host organism, in order to induce an immune response. To evaluate whether BTV1 delta VP6 can express viral proteins wildtype BSR cells were used as a proxy for the mammalian host. Detection of the non-structural protein, NS2, was used as a marker for viral protein expression. In a comparison of the protein expression of the BTV1 delta VP6 virus with wildtype BTV-1 the NS2 protein was expressed at increasing levels with time in both BTV1 delta VP6 infected BSR and BTV-1 infected BSR (FIG. 15). The level of protein expression from the BTV1 delta VP6 virus was lower than that for wildtype BTV-1, as would be expected for a defective virus. This data demonstrates that the BTV1 delta VP6 virus expresses virus protein in non-complementing BSR cells.

Marker antigens can be added to the BTV genome. The ability to express a marker antigen/peptide from the BTV genome would allow a DIVA compliant vaccine strain to be created (DIVA: differentiating infected from vaccinated animals). To demonstrate that this is possible using the reverse genetics approach in combination with complementing cell lines, a clone containing an in frame fusion of NS3 with eGFP was made, pBTV1 S10GFP. A complete genomic set of in vitro synthesised T7 transcripts was made as previously described, but containing the NS3-eGFP fusion transcript instead of the wildtype segment 10 transcript. The corresponding mutant virus, BTV1 S10GFP, was recovered as described, using a BSR NS3 complementing cell line in the place of wildtype BSR cells during transfection. When non-complementing C6/36 cells were infected with BTV1 S10GFP the expression of eGFP was confirmed by its fluorescence under UV light (data not shown)

Figure 16:
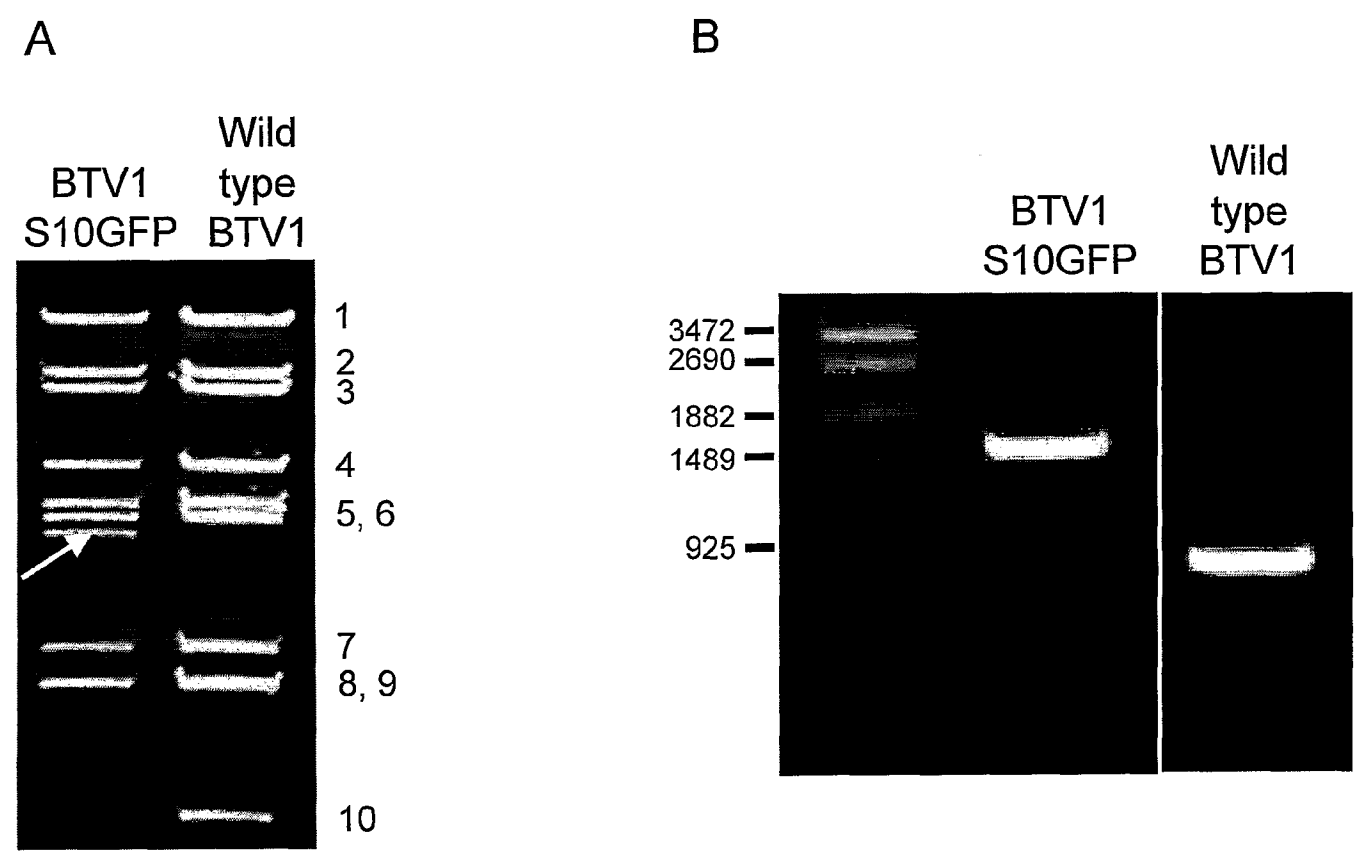
Figure 17:
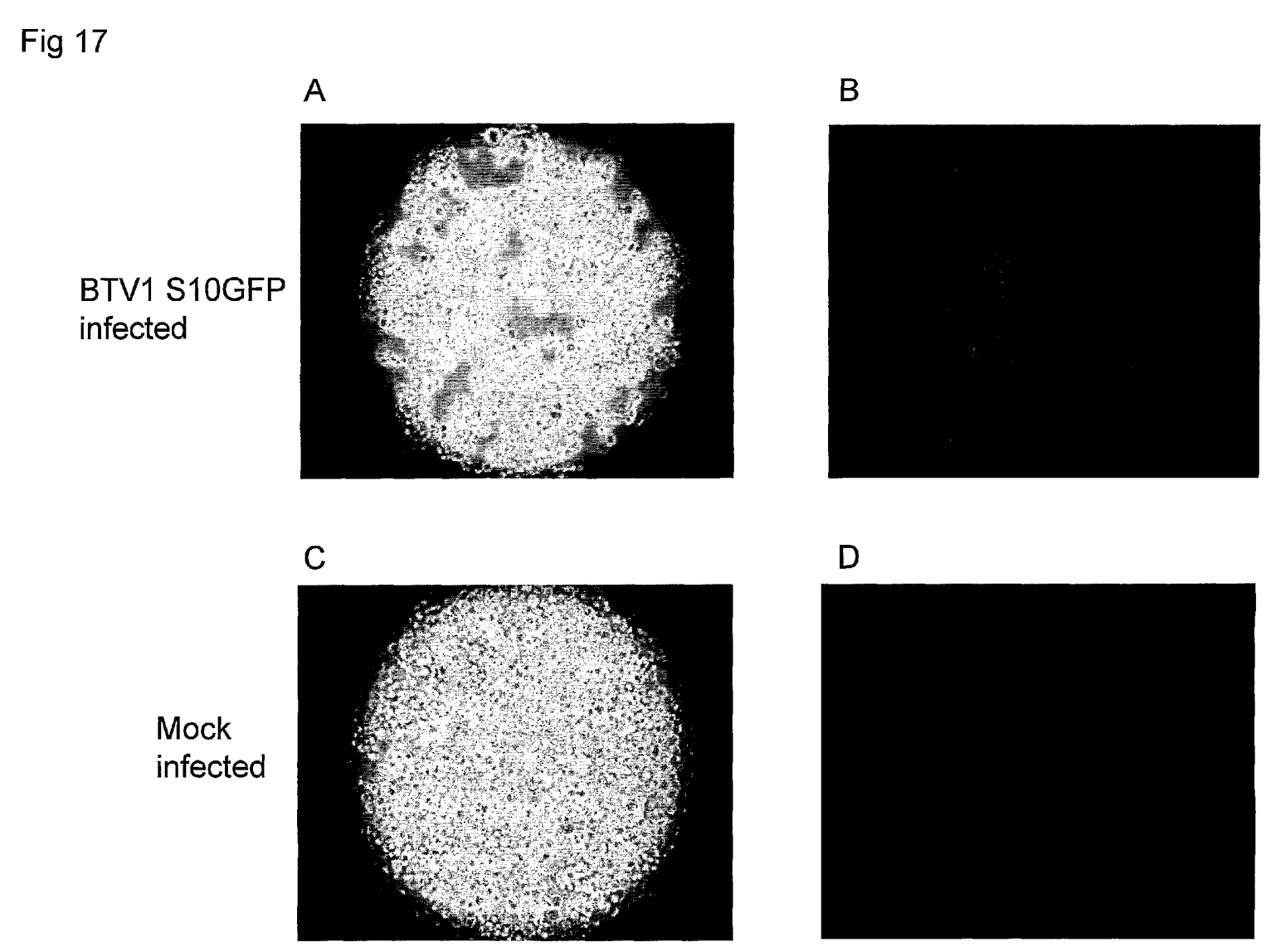

Characterisation of genome segment 10 of BTV1 S10GFP. The genome of BTV1 S10GFP lacks the wild type S10 segment and contains a bigger segment, corresponding to the S10 GFP fusion (FIG. 16A). The S10 segment from BTV1 S10GFP was amplified by RT-PCR using primers annealing at the ends of the S10 segment (BTV1S10T7 EcoRI and NS3BsmBi rev), and the expected product of 1446 nt was amplified (FIG. 16B). The RT-PCR product from BTV1 S10GFP was sequenced and the presence of the eGFP gene was confirmed (see FIG. 17), demonstrating that the virus recovered was constructed correctly.

Increased Efficiency of Virus Recovery from Plasmid-derived Transcripts

Two changes which increase the efficiency of the bluetongue virus recovery from plasmid-derived T7 transcripts have been made. Both of these changes are alterations to the transfection method described above. Each improvement results in a ~10 fold increase in the efficiency of recovering virus from plasmid-derived transcripts, and together result in ~100 fold increase in the recovery of virus.

Figure 18:
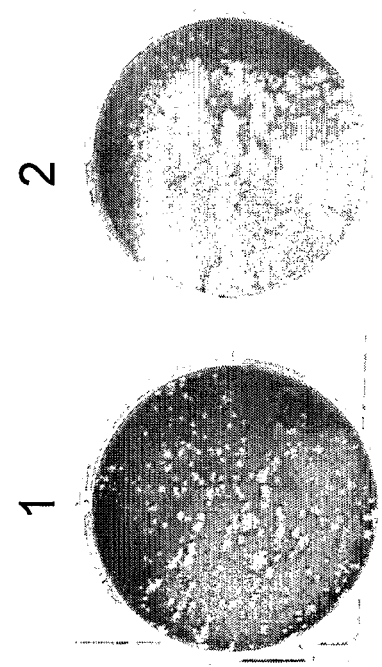
FIG. 18 shows that double transfection increases the recovery of virus from core derived transcripts. Confluent BSR cell monolayers were transfected once (well 1) or twice (well 2) with 200 ng viral ssRNA synthesised from BTV cores. Wells were overlaid with agarose as described herein.
Figure 19:
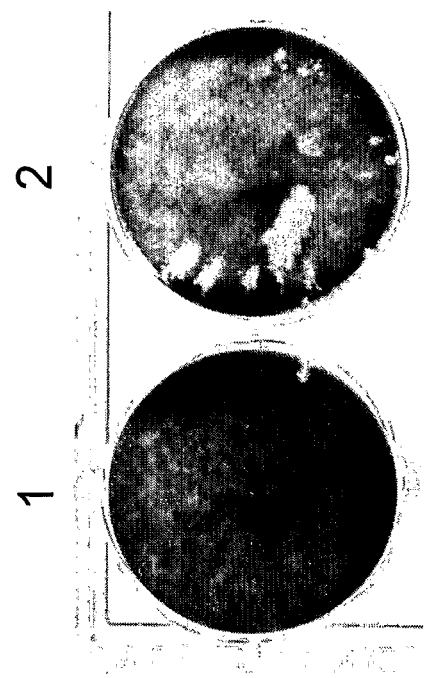
FIG. 19 shows that double transfection increases the recovery of virus from plasmid-derived transcripts. Confluent BSR cell monolayers were transfected once (well 1) or twice (well 2) with 2 µg of plasmid-derived T7 transcripts. Wells were overlaid with agarose as described herein.

Modification #1, Double Transfection:

The cells are transfected twice (instead of once), with a complete set of ten plasmid derived transcripts on each occasion, as described above. The transfections are performed 18 hours apart, and result in an increase in virus recovery of ~10 fold, over using a single transfection. The increase in recovery of virus using the double transfection method was observed when using ssRNA made from BTV cores (FIG. 18) and when using a complete set of T7 transcripts made from ten cDNA clones (FIG. 19).

Modification #2, Omission of Genome Segments 2, 5, 7, and 10 from the First Transfection:

The cells are transfected twice, as in modification #1, but the T7 transcripts encoding genome segments 2, 5, 7, and 10 are omitted from the first transfection. The second transfection uses a complete set of ten transcripts. The transfections are performed 18 hours apart, and result in a further increase in virus recovery of ~10 fold over using the double transfection described above (FIG. 20).

Discussion

The two approaches described represent alternative reverse genetics systems for BTV, using either a mixture of authentic viral transcripts and T7 transcripts, or a complete genomic set of T7 transcripts. They extend the discovery that BTV transcripts are infectious when used to transfect permissive cells [1], and demonstrate that in vitro synthesized T7 transcripts with a cap analogue at the 5' end can functionally substitute for transcripts synthesized by core particles.

The recovery of progeny virus with genome segments originating from two separate core-derived mRNA preparations established the principle of introducing exogenous transcripts into the genome of BTV by mixing with authentic viral transcripts (FIG. 1B). The observation that mixing the mRNA preparations after transcription was effective in producing reassortants allowed for the possibility of using plasmid-derived transcripts in combination with core-derived mRNAs to introduce targeted mutations into the BTV genome. The introduction of the BTV-10 segment 10 transcript into the genome of BTV-1 was investigated to determine whether the facile introduction of plasmid-derived transcripts into infectious BTV could be achieved.

Figure 3:
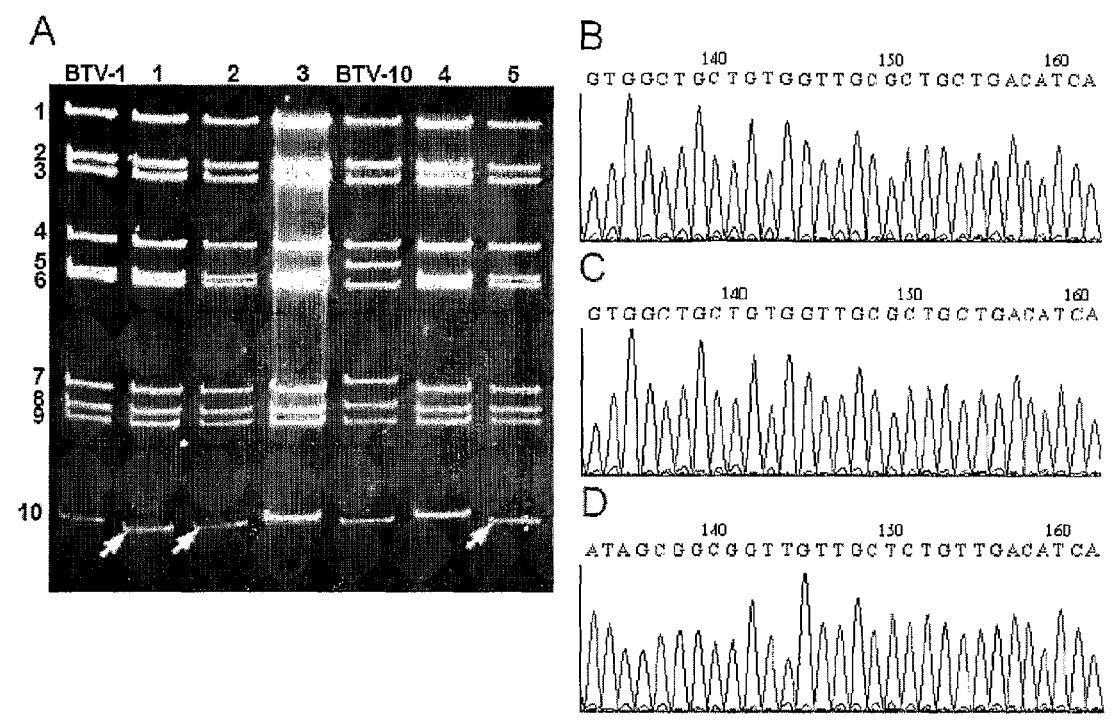
Figure 4:
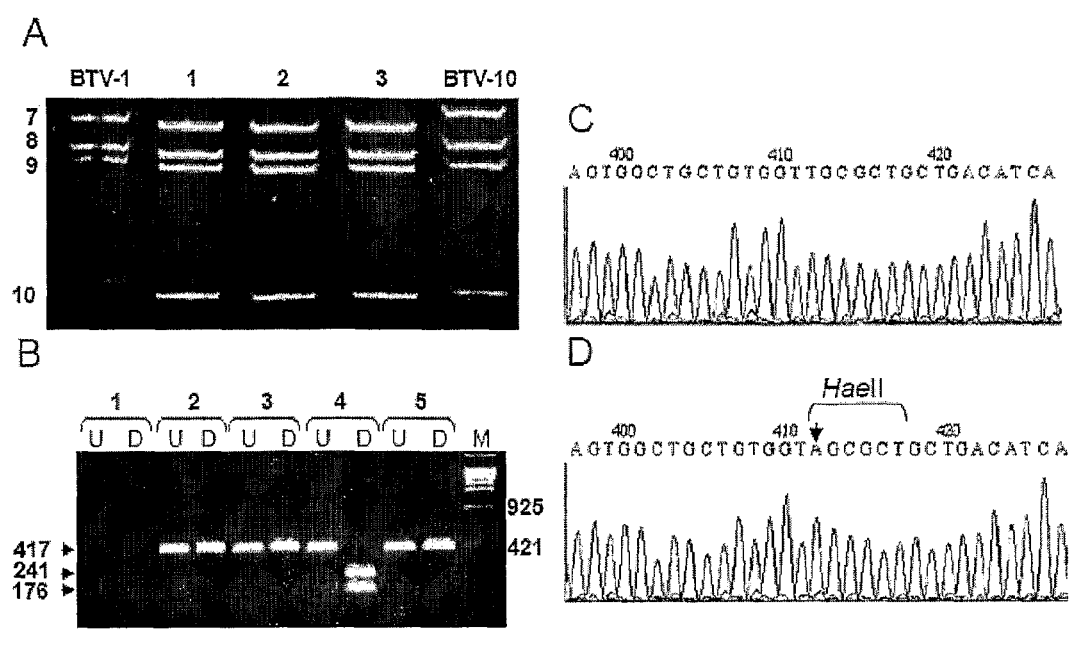

This model system showed that using an excess of the T7 transcript generated reassortant plaques at a frequency which made the screening of individual plaques practical (15-80%). The initial screening of plaques by the rate of migration of the segment 10 dsRNA on PAGE gels (FIG. 3) was confirmed by sequencing of the RT-PCR product (FIG. 3). The high efficiency of reassortment between the T7 transcript and authentic viral transcripts has meant that a selectable marker approach was not required. The introduction of the HaeII site marker mutation into segment 10 of BTV confirmed that reassortants were derived from the in vitro synthesized segment 10 T7 transcript (FIG. 4). The HaeII-containing segment 10 was recovered with a similar efficiency to wildtype BTV-10 segment 10. Both segment 10 reassortant viruses demonstrated no gross replication deficiency compared to wildtype BTV-1 (data not shown). This shows that genome segment 10 from BTV-10 is functionally compatible with a background of BTV-1 genome segments both at the levels of RNA packaging and replication, and NS3/NS3A protein function.

Figure 5:
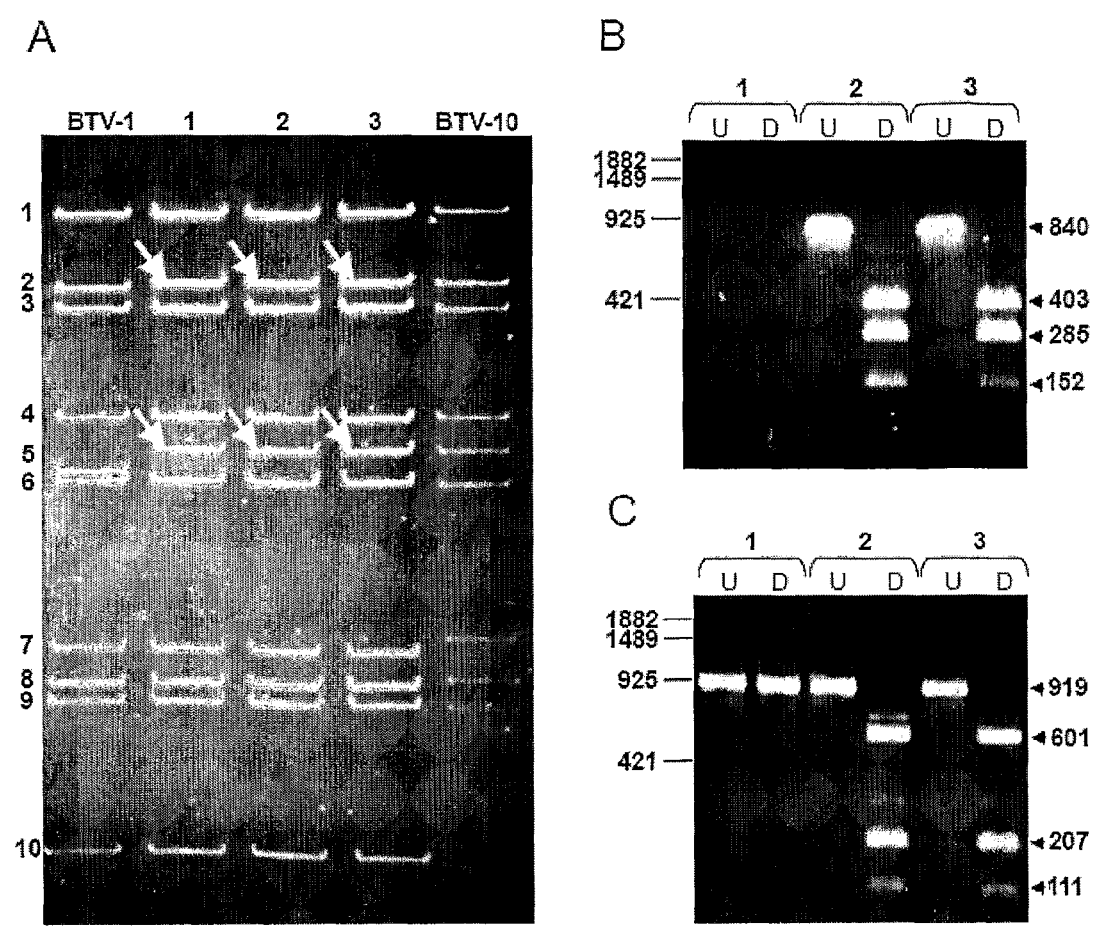

The simultaneous reassortment of two T7 transcripts into the BTV genome to replace the antigenically important outer capsid proteins of BTV-1 with those from BTV-10 cDNA clones was shown to be possible using an excess of both T7 transcripts (FIG. 5). Progeny plaques containing the BTV-10 segment 2 and 5 were recovered at a 20-80% frequency, but no reassortants were isolated containing only segment 2 or segment 5 from BTV-10. This demonstrates that together segments 2 and 5 of BTV-10 can functionally substitute for the corresponding BTV-1 genome segments, and suggests there is incompatibility between segment 2 and segment 5 from these two serotypes at some level. The encoded proteins, VP2 and VP5, are highly variable due their exposure to immune selective pressure on the surface of the virus particle. Our favoured explanation is that the VP2 and VP5 proteins have co-evolved and that the three dimensional structure of VP2 from one serotype is not necessarily compatible with the VP5 from another serotype. This is consistent with the previously reported incompatibility of the VP2 and VP5 proteins from some serotype combinations observed in the generation of BTV virus-like particles [23, 24]. Incompatibility of segment 2 and segment 5 in some serotype combinations at an RNA packaging level is another possibility. The simultaneous introduction of both outer capsid proteins from another serotype allows the possibility of producing vaccine strains to different serotypes based on a consistent genetic background. The high amino acid sequence divergence between the VP2 proteins of BTV-1 and BTV-10 (40% amino acid identity) suggest that the assembly of varied VP2+VP5 pairs onto the conserved core of the BTV virion will be possible.

The recovery of BTV-1 from a complete set of T7 transcripts was investigated to determine whether virus with a fully defined genome could be recovered from cDNA clones.

Figure 7:
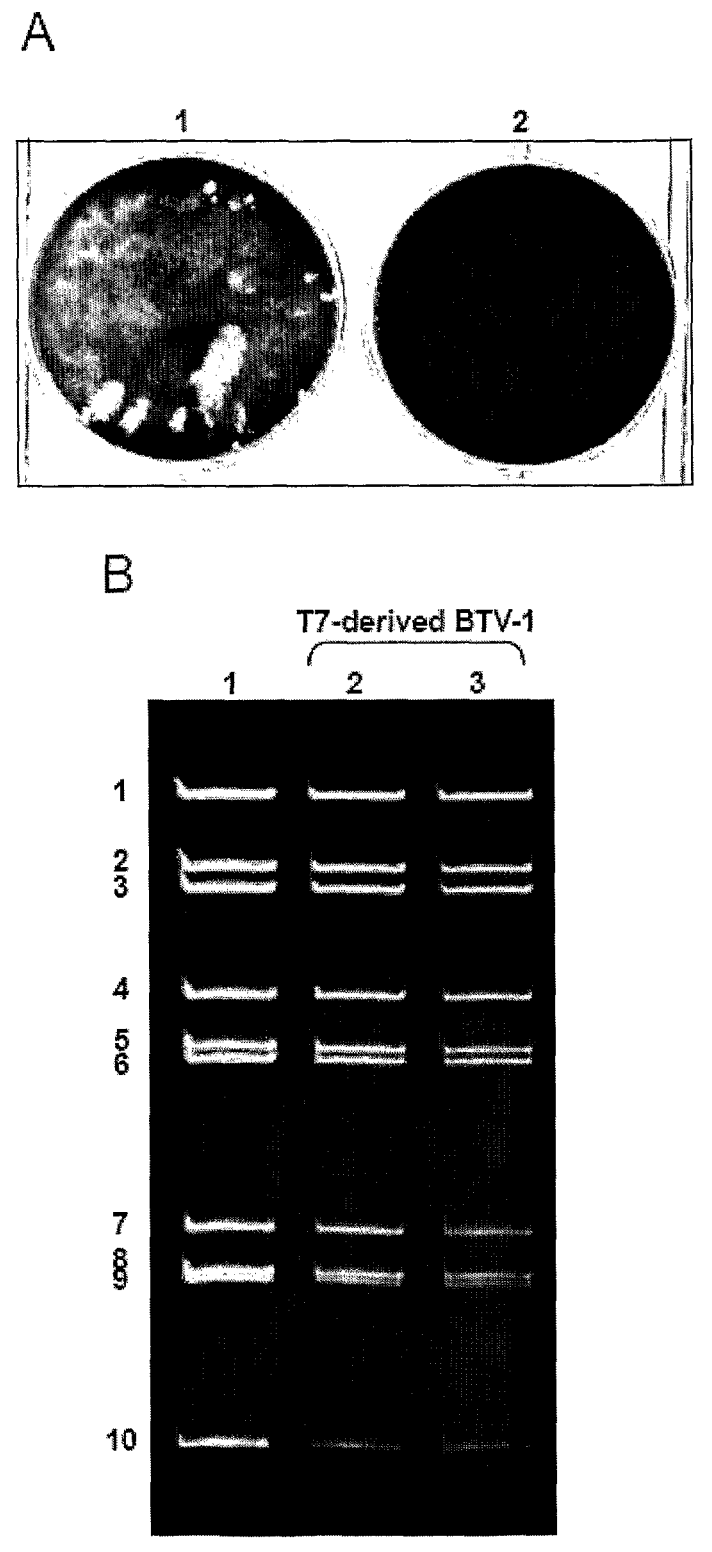
Figure 9:
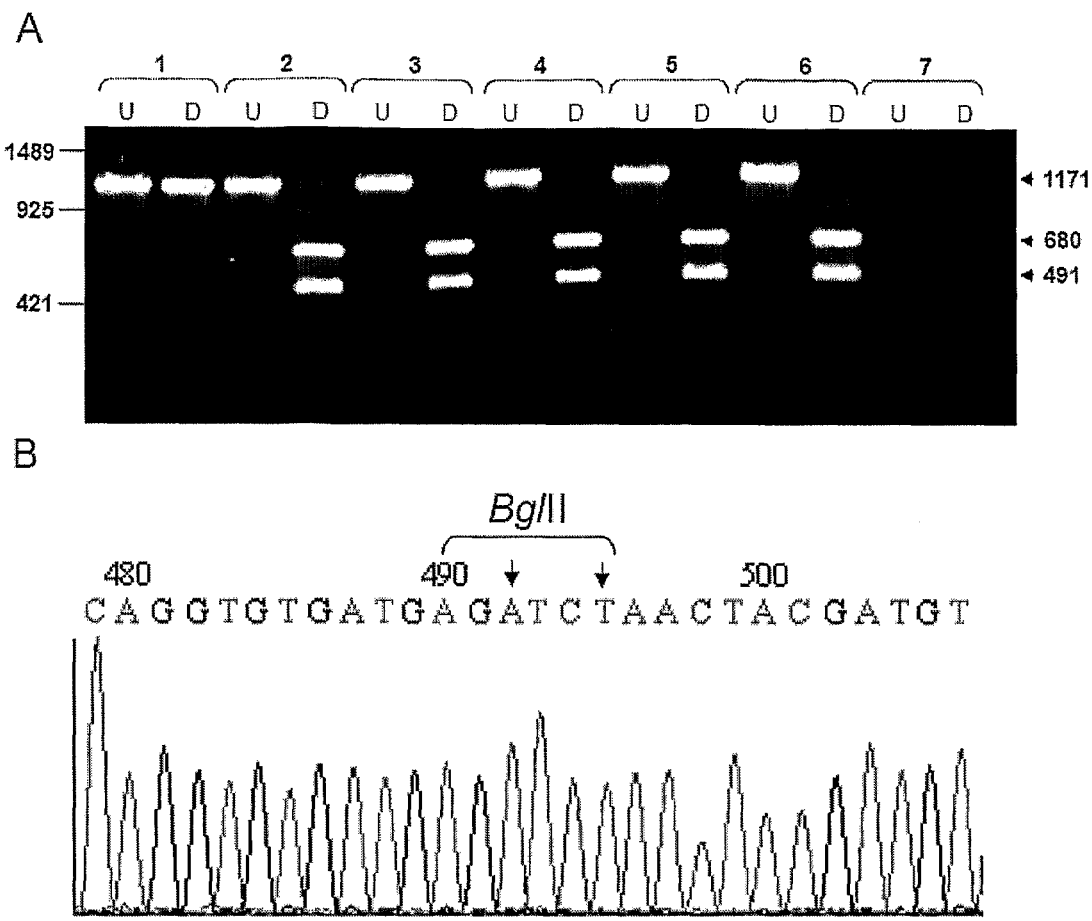
FIG. 9 shows detection of an introduced marker mutation in BTV-1 generated from ten T7 transcripts. (A). BglII digestion of segment 8 RT-PCR products. BglII-digested 20 RT-PCR products amplified from genomic dsRNA using segment 8 primers NS2_Bam_T7_F and NS2_Bam_R, and separated on 1% agarose gels. U=undigested RT-PCR product, D=BglII digested RT-PCR product. Lanes 1, wildtype BTV-1 , lanes 2-6, five separate plaques derived from transfection including the segment 8 BglII mutant transcript, lanes 7, no template. StyI-digested phage λ DNA marker sizes in bp indicated on left. Size of RT-PCR product and digest fragments indicated on right in bp. (B). Sequence electropherogram of segment 8 RT-PCR product from transfection including the segment 8 BglII mutant transcript (SEQ ID NO: 25). Segment 8 target sequence from total viral dsRNA was amplified by RT-PCR using the primers described in panel A. The amplified target was sequenced using BTV1_S8_627R. Arrows indicates the introduced point mutations.

Transfection of BSR monolayers with the ten T7 transcripts was found to lead to the production of plaques (FIG. 7). The recovery of a BglII marker mutation into the S8 segment confirmed that the virus recovered was derived from the T7 transcripts used in the transfections (FIGS. 8 and 9). The recovery of infectious BTV from T7 transcripts alone demonstrates that T7 transcripts synthesized in the presence of cap analogue are functionally equivalent to authentic viral transcripts at all stages of the replication cycle. The T7 transcripts must be translated, selected during genome packaging, and act as templates for negative strand synthesis if virions are to be generated. Furthermore, after negative strand synthesis the resulting dsRNA genome segment must be competent for transcription in the next round of infection. The recovery of BTV from T7 transcripts leads to the recovery of ~100 fold less plaques than when an equivalent quantity of core-derived viral transcripts are used. The lower efficiency may derive from the fact that only a proportion of T7 transcripts generated in the presence of a cap analogue have the cap analogue incorporated at the 5' end. In addition to being poorly translated the uncapped transcripts may be defective during RNA packaging, negative strand synthesis or during transcription in the next round of infection. Importantly the uncapped transcripts have a 5' triphosphate moiety which is known to be a pathogen-associated molecular pattern (PAMP) recognised by RIG-I and leading to the induction of antiviral responses [25-28]. Alternatively, the technical issues associated with generating ten ssRNA molecules with the conserved terminal sequences intact may contribute to the lower recovery observed with T7 transcripts.

The recovery of BTV entirely from plasmid-derived transcripts allows the generation of BTV mutants with a consistent genetic background. This approach will be useful in the recovery mutants which are expected to have a slow replication phenotype, as the screening of plaques for the desired mutant among wildtype plaques is not required. In such cases there would be no background of faster replicating virus which may hamper the recovery of the slower replicating mutants. This approach could also be used to recover primary/low passage isolates of BTV, avoiding gradual alteration of these strains to cell culture conditions. The recovery of reassortants containing one plasmid-derived genome segment requires the construction of a single clone or PCR product and is applicable to any genome segment. This single construct approach can be used to investigate individual viral genes without the need to construct a full set of ten clones. As Reoviridae members have a common replication strategy both the reassortment and T7 only reverse genetics approaches may be applicable to a wide range of viruses which lack a reverse genetics system. The use of in vitro synthesized T7 transcripts in both approaches obviates the requirement to supply T7 RNA polymerase by infecting with a recombinant poxvirus, which may interfere with the replication of the virus being recovered.

Alternative reverse genetics strategies have been used successfully for other genera in the Reoviridae [2-4]. The first reverse genetics system was a helper virus system for the mammalian orthoreoviruses [3]. This approach combined reovirus infection of permissive cells and transfection with viral dsRNA, viral mRNA, a T7 transcript, and in vitro translated viral mRNA. Another helper virus approach has allowed the replacement of a rotavirus outer capsid protein with the corresponding protein from another serotype [2]. The expression of the introduced genome segment was driven in vivo by the recombinant T7 vaccinia virus system, and selective pressure against the equivalent helper virus protein was provided by the use of antibody selection. Most recently mammalian orthoreovirus has been recovered using a plasmid-based system similar to the T7 driven systems first used with negative strand viruses [4]. In this case expression of all ten genome segments was driven in vivo by the recombinant T7 vaccinia virus system. All the successful reverse genetics strategies have several notable features in common; 1) The genome segments derived from cDNA clones are provided as message sense transcripts in the transfected cell. 2) The cDNA-derived transcripts used have the same 5' end and 3' end sequences as the corresponding viral transcript. The 5' ends are generated through the use of a T7 promoter with the appropriate sequence, and the 3' ends are generated through the use of the hepatitis delta ribozyme in vivo or a restriction enzyme site in vitro. All genome segments in Reoviridae members have short conserved sequences at their extreme 5' and 3' ends the functions of which are still being elucidated. 3) Like the authentic viral transcripts the cDNA-derived transcripts are capped, either in vitro with a cap analogue or in vivo through the cross-capping activity associated with the vaccinia T7 RNA polymerase recombinant [13]. To achieve infectious virus recovery gene expression must be sufficient to allow the assembly of progeny core particles, which themselves are transcriptionally active and lead to an amplification of gene expression. A high level of gene expression is needed to assemble these incomplete virions, and without the presence of the cap structure at the 5' end of the cDNA-derived transcripts their stability and level of translation would much reduced [14].

Figure 12:
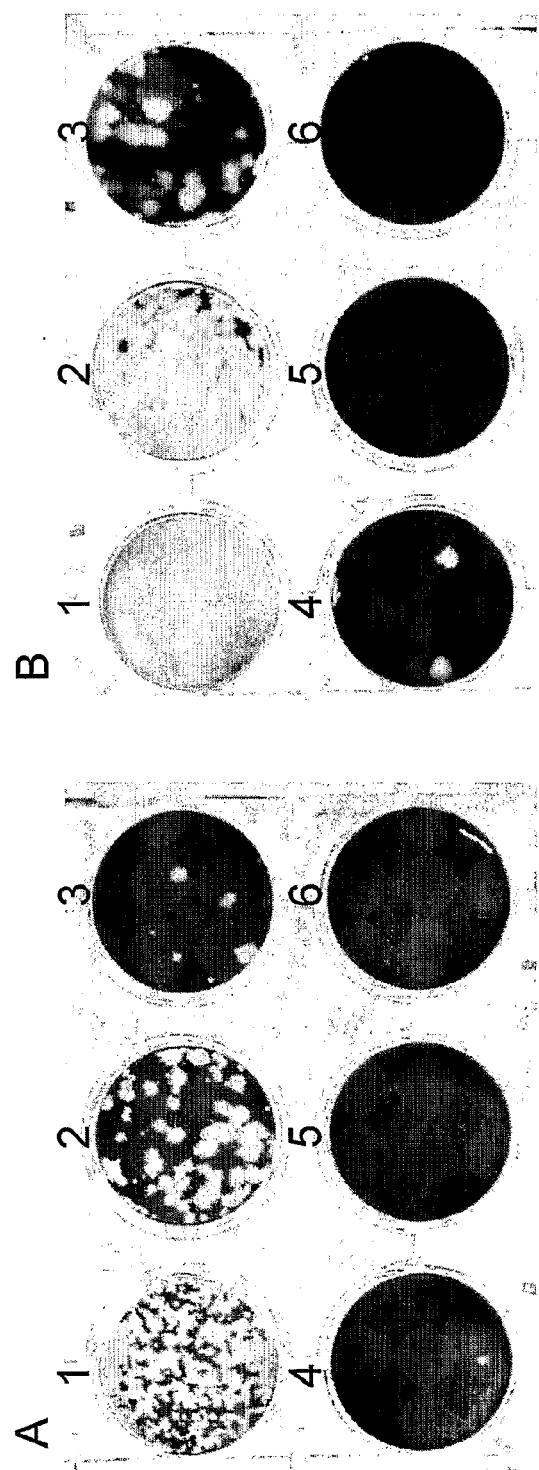
FIG. 12 shows that BTV1 delta VP6 produces plaques in the complementing BSR VP6 cell line. Ten-fold dilutions of virus stocks were used to infect confluent cell monolayers from well 1 to well 6. The infected monolayers were overlaid with solid medium and stained with Crystal Violet after 72 hours. (A) BSR VP6 cells infected with BTV1 delta VP6. (B) Wildtype BSR cells infected with wildtype BTV-1.

DISC viruses lacking a viral gene have been generated using the combination of the BTV reverse genetics system and complementing cell lines. The viruses recovered fulfil the following criteria for a BTV DISC virus vaccine strain: 1) The expression of viral proteins in non-complementing mammalian cells (FIG. 15); 2) No detectible infectious virus generated in non-complementing mammalian or insect cell lines (FIG. 14); and 3) Robust replication in the corresponding complementing cell line (FIG. 12). Additionally, the ability to express foreign proteins or peptides has been demonstrated using the insertion of the eGFP protein into the NS3 open reading frame, allowing the production of vaccine strains containing an immunological marker which may be detected in vaccinated animals to distinguish them from infected animals, the DIVA concept (distinguishing infected and vaccinated animals).

The T7 transcripts or viral ssRNA have two functions in the replication cycle of members of the Reoviridae family; 1) to be translated to generate the viral proteins; and 2) to act as replication intermediates for the synthesis of new double-stranded genome segments. For rescue to be successful in a cell, using the single transfection approach, a proportion of the transcripts must remain available to be packaged and replicated in assembling progeny virus particles. This is expected to be a limiting step in the efficiency of virus recovery, as unlike a normal infection new transcripts are not being continually synthesised from an infecting core particle. To increase the efficiency of recovery a second transfection was performed to introduce additional transcripts for packaging at a time when morphogenesis would be expected to have reached the packaging stage. The predicted increase in the recovery of virus was observed using viral ssRNA or T7 transcripts (FIGS. 18 and 19), and was found to be ~10 fold.

Figure 20:
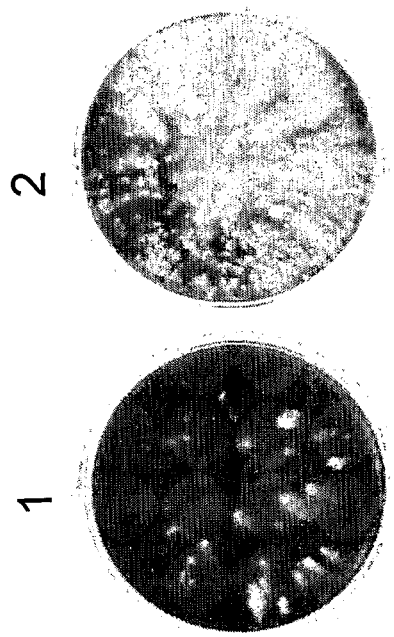
FIG. 20 shows that omission of genome segments 2, 5, 7, and 10 from the first transfection increases the recovery of virus from plasmid-derived transcripts. Confluent BSR cell monolayers were transfected with a complete complement of ten T7 transcripts (well 1) or a set of T7 transcripts lacking segments 2, 5, 7, and 10 (well 2), in the first transfection. Both wells were transfected with a complete complement of ten T7 transcripts in the second transfection. 100 ng of each T7 transcript was used in both transfections.

To further increase efficiency of recovery genome segments were omitted from the first transfection so that morphogenesis could not proceed beyond the assembly of the inner layer of the capsid. This approach was adopted to arrest assembly at the stage where packaging is expected to occur. The genome segment coding assignments for the omitted segments are: segment 2 encodes VP2 (outer capsid), segment 5 encodes VP5 (outer capsid), segment 7 encodes VP7 (middle layer of capsid), and segment 10 encodes NS3 (required for virus egress). The consequence of omitting segments 2, 5, 7, and 10 is that the middle layer and outer layer of the triple layered capsid are not synthesised, and the egress protein NS3 is not present. It was found that arresting morphogenesis in this way increased the recovery of virus a further ~10 fold when a complete set of ten transcripts was provided in the second transfection. (FIG. 20).

Together these two improvements to the transfection protocol result in a ~100 fold increase in virus recovery over using a single transfection, allowing the reliable recovery of wildtype or mutant viruses. These improvements have allowed the reliable recovery of inherently defective viruses using complementing cell lines.

Reverse genetics, as with other viruses, can contribute to the understanding of BTV in several research areas. The ability to recover specific mutations into the genome of BTV using either system not only provides a novel tool for the molecular dissection of BTV and related orbiviruses, but also the opportunity to develop specifically attenuated vaccines to these viruses. The investigation of BTV protein function to date has mainly been based on recombinant protein expression. The ability to introduce specific mutations into the genes of BTV will further our understanding of the functions of the viral proteins in replicating virus, and allow the corroboration of functions already assigned. The cis-acting RNA sequences that control the replication, packaging, and expression of Orbivirus genomes remain unmapped, and are poorly understood. Reverse genetics allows mapping of these regulatory sequences and can assist in the investigation of how they act. The replacement of outer capsid proteins can be used to generate vaccine strains to different serotypes based on a common genetic background. Moreover, it will be possible to identify determinants of pathogenicity of BTV and related orbiviruses, and design multiply attenuated vaccine strains.

References

1. Boyce, M. and Roy, P. 2007. Recovery of Infectious Bluetongue Virus from RNA. *J. Vivol.* 81(5): 2179-2186.
2. Komoto, S., J. Sasaki, and K. Taniguchi. 2006. Reverse genetics system for introduction of site-specific mutations into the double-stranded RNA genome of infectious rotavirus. *Proc. Natl. Acad. Sci. USA* 103:4646-4651.
3. Roner, M. R., and W. K. Joklik. 2001. Reovirus reverse genetics: incorporation of the CAT gene into the reovirus genome. *Proc. Natl. Acad. Sci. USA* 98:8036-8041.
4. Kobayashi, T., et al. 2007 A Reverse Genetics System for dsRNA Viruses. *Cell Host & Microbe.* 1(2):147-157.
5. Roy, P., Towards the control of emerging Bluetongue disease. 1991, *London: Oxford Virology.* 1-71.
6. Patton, J. T., Rotavirus VP1 alone specifically binds to the 3' end of viral mRNA, but the interaction is not sufficient to initiate minus-strand synthesis. *J. Virol.*, 1996. 70(11): p. 7940-7.
7. Patton, J. T., et al., cis-Acting signals that promote genome replication in rotavirus mRNA. *J. Virol.*, 1996. 70(6): p. 3961-71.
8. Poncet, D., C. Aponte, and J. Cohen, Rotavirus protein NSP3 (NS34) is bound to the 3' end consensus sequence of viral mRNAs in infected cells. *J. Virol.*, 1993. 67(6): p. 3159-65.
9. Chizhikov, V. and J. T. Patton, A four-nucleotide translation enhancer in the 3'-terminal consensus sequence of the non-polyadenylated mRNAs of rotavirus. *RNA*, 2000. 6(6): p. 814-25.
10. Roner, M. R., K. Bassett, and J. Roehr, Identification of the 5' sequences required for incorporation of an engineered ssRNA into the Reovirus genome. *Virology*, 2004. 329(2): p. 348-60.
11. Roner, M. R. and J. Roehr, The 3' sequences required for incorporation of an engineered ssRNA into the Reovirus genome. *Virol J*, 2006. 3: p. 1.
12. Roner, M. R. and B. G. Steele, Localizing the reovirus packaging signals using an engineered m1 and s2 ssRNA. *Virology*, 2007. 358(1): p. 89-97.
13. Fuerst, T. R. and B. Moss, Structure and stability of mRNA synthesized by vaccinia virus-encoded bacteriophage T7 RNA polymerase in mammalian cells. Importance of the 5' untranslated leader. *J Mol Biol*, 1989. 206(2): p. 333-48.
14. Muthukrishnan, S., et al., 5'-Terminal 7-methylguanosine in eukaryotic mRNA is required for translation. *Nature*, 1975. 255: p. 33-37.
15. Wirblich, C., B. Bhattacharya, and P. Roy, Nonstructural protein 3 of bluetongue virus assists virus release by recruiting ESCRT-I protein Tsg101. *J. Virol.* 2006. 80(1): p. 460-73.
16. Bhattacharya, B., R. J. Noad, and P. Roy, Interaction between Bluetongue virus outer capsid protein VP2 and vimentin is necessary for virus egress. *Virol J*, 2007. Jan. 15; 4:7.
17. Weiner M. P., C., G. L., Schoelttin, W., Cline, J., Mathur, E., amd Bauer, J. C., Site directed mutagenesis of double stranded DNA by the polymerase chain reaction. *Gene*, 1994. 151: p. 119-123.
18. Maan, S., S. Rao, N. S. Maan, S. J. Anthony, H. Attoui, A. R. Samuel, and P. P. Mertens. 2007. Rapid cDNA synthesis and sequencing techniques for the genetic study of bluetongue and other dsRNA viruses. *J. Virol. Methods* 143: 132-9.
19. Sambrook, J., and D. W. Russell. 2001. Molecular Cloning: a laboratory manual, 3rd ed. Cold Spring Harbour Laboratory Press, Cold Spring Harbour, NY.
20. Sanger, F., S, Nicklen, and A. R. Coulson. 1977. DNA sequencing with chain-terminating inhibitors. *Proc. Natl. Acad. Sci. U.S.A.* 74:5463-7.
21. Kahlon, J., K. Sugiyama, and P. Roy. 1983. Molecular basis of bluetongue virus neutralization. *J. Virol.* 48:627-32.
22. Yanisch-Perron, C., J. Vieira, and J. Messing. 1985. Improved M13 phage cloning vectors and host strains: nucleotide sequences of the M13 mp 18 and pUC19 vectors. *Gene* 33:103-19.
23. Loudon, P. T., T. Hirasawa, S. Oldfield, M. Murphy, and P. Roy. 1991. Expression of the outer capsid protein VP5 of two bluetongue viruses, and synthesis of chimeric double-shelled virus-like particles using combinations of recombinant baculoviruses. *Virology* 182:793-801.
24. Roy, P., B. D. H. L., H. LeBlois, and B. J. Erasmus. 1994. Long-lasting protection of sheep against bluetongue challenge after vaccination with virus-like particles: Evidence for homologous and partial heterologous protection. *Vaccine* 12:805-811.
25. Cui, S., K. Eisenacher, A. Kirchhofer, K. Brzozka, A. Lammens, K. Lammens, T. Fujita, K. K. Conzelmann, A. Krug, and K. P. Hopfner. 2008. The C-terminal regulatory domain is the RNA 5'-triphosphate sensor of RIG-I. *Mol. Cell.* 29:169-79.

26. Hornung, V., J. Ellegast, S. Kim, K. Brzozka, A. Jung, H. Kato, H. Poeck, S. Akira, K. K. Conzelmann, M. Schlee, S. Endres, and G. Hartmann. 2006. 5'-Triphosphate RNA is the ligand for RIG-I. *Science* 314:994-7.
27. Pichlmair, A., O, Schulz, C. P. Tan, T. I. Naslund, P. Liljestrom, F. Weber, and C. Reis e Sousa. 2006. RIG-1-mediated antiviral responses to single-stranded RNA bearing 5'-phosphates. *Science* 314:997-1001.
28. Plumet, S., F. Herschke, J. M. Bourhis, H. Valentin, S. Longhi, and D. Gerlier. 2007. Cytosolic 5'-triphosphate ended viral leader transcript of measles virus as activator of the RIG I-mediated interferon response. PLoS ONE 2:e279.
29. Tani, H. et al., Replication-competent recombinant vesicular stomatitis virus encoding hepatitis C virus envelope proteins. *J Virol* 81 (16), 8601 (2007).

The invention claimed is:

1. A method for producing a vaccinal viral strain of a virus which is a member of the Reoviridae family, the method comprising:
   introducing a mutation into the Reoviridae virus so that the function of an essential gene is destroyed;
   transfecting a cell with viral single stranded RNA (ss RNA) derived from the virus genome and comprising the mutation, wherein the transfection does not use a helper virus, and wherein transfecting the cell comprises two or more transfection steps, wherein:
   (1) a first transfection step comprises transfecting the cell with ss RNA encoding components required for assembly of an inner viral capsid layer; and
   (2) a second transfection step comprises transfecting the cell with ss RNA which is a transcript of the viral genome and comprises the mutation, and encodes all the components required for assembly of the virus; and
   culturing the transfected cell under suitable conditions in order to lead to the production of the vaccinal viral strain,
   wherein the cell complements the function of the essential viral gene thereby allowing the vaccinal viral strain to replicate in the cell.

2. The method of claim 1, wherein there is a time gap of at least 6 hours between the first and second transfection steps.

3. The method of claim 1, wherein the virus is a member of the Rotavirus or Orbivirus genus.

4. The method of claim 1, wherein the virus is bluetongue virus, African horse sickness virus or epizootic hemorrhagic disease virus.

5. The method of claim 1, wherein part of the ss RNA is a transcript of a cDNA clone of the viral genome comprising the mutation.

6. The method of claim 1, wherein all the ss RNA is a transcript of a cDNA clone of the viral genome comprising the mutation.

7. The method of claim 1, wherein the function of more than one essential gene is destroyed.

8. The method of claim 1, wherein the essential gene encodes a polymerase, helicase, capping enzyme or a non-structural protein.

9. The method of claim 1, wherein the cell is suitable for being transfected with ss RNA and for culturing viral strains.

10. The method of claim 1, wherein the viral ss RNA used to transfect the cell is isolated ss RNA.

11. The method of claim 1, further comprising isolating the vaccinal viral strain from the cell.

12. A method for producing a modified viral strain of a virus which is a member of the Reoviridae family, the method comprising:
   introducing a modification into the Reoviridae virus;
   transfecting a cell with viral single stranded RNA (ss RNA) derived from the virus genome and comprising the modification, wherein the transfection does not use a helper virus, and wherein transfecting the cell comprises two or more transfection steps, wherein:
   (1) a first transfection step comprises transfecting the cell with ss RNA encoding components required for assembly of an inner viral capsid layer; and
   (2) a second transfection step comprises transfecting the cell with ss RNA which is a transcript of the viral genome and comprises the modification, and encodes all the components required for assembly of the virus; and
   culturing the transfected cell under suitable conditions in order to lead to the production of the modified viral strain,
   wherein the cell allows the modified viral strain to replicate in the cell.

13. The method of claim 12, wherein there is a time gap of at least 6 hours between the first and second transfection steps.

14. The method of claim 9, wherein the cell is a BHK 21 cell, a Vero cell, a 293T cell, a BSR cell, a HeLa cell, a C6/36 cell or a KC cell.

* * * * *